US006767707B2

(12) United States Patent
Venta et al.

(10) Patent No.: US 6,767,707 B2
(45) Date of Patent: **\*Jul. 27, 2004**

(54) DNA ENCODING CANINE VON WILLEBRAND FACTOR AND METHODS OF USE

(75) Inventors: Patrick J. Venta, Pinckney, MI (US); George J. Brewer, Ann Arbor, MI (US); Vilma Yuzbasiyan-Gurkan, Ann Arbor, MI (US); William D. Schall, Williamston, MI (US)

(73) Assignee: University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/886,900

(22) Filed: Jun. 21, 2001

(65) Prior Publication Data

US 2002/0137051 A1 Sep. 26, 2002

Related U.S. Application Data

(63) Continuation of application No. 09/662,478, filed on Sep. 15, 2000, which is a continuation-in-part of application No. 08/896,449, filed on Jul. 18, 1997, now Pat. No. 6,040,143.
(60) Provisional application No. 60/020,998, filed on Jul. 19, 1996.

(30) Foreign Application Priority Data

Aug. 10, 1999 (WO) ............................... PCT/US99/18153

(51) Int. Cl.$^7$ ........................... C12Q 1/68; C12P 19/34; C07H 21/00; C07H 21/04
(52) U.S. Cl. ........................ 435/6; 435/91.2; 536/22.1; 536/24.31
(58) Field of Search ........................... 536/22.1, 24.31; 435/6, 91.2

(56) References Cited

U.S. PATENT DOCUMENTS

| 5,843,649 A | * 12/1998 | Stoerker et al. | 435/6 |
| 6,040,143 A | * 3/2000 | Venta et al. | 435/6 |
| 6,074,832 A | * 6/2000 | Venta et al. | 435/6 |

FOREIGN PATENT DOCUMENTS

| EP | 197592 A1 | 10/1986 | ........... C12N/15/00 |
| WO | WO 96/15262 A2 | 5/1996 | ............ C12Q/1/68 |
| WO | WO 98/03683 A1 | 1/1998 | |

OTHER PUBLICATIONS

Shibuya et al., "A polymorphic (AGGAAT) n tandem repeat in an intron of the canine von Willebrand factor gene", Animal Genetics , vol. 25, pp 122 (1994).*
Bartlett et al., "Mutation segregation and rapid carrier detection of X–linked muscular dystrophy in dogs", AJVR, vol. 57, No. 5, pp 650–654 (1996).*
Nucleic acid sequence search report, accession X04385.*

Avgeris, S. et al. "Plasma von Willebrand Factor Concentration and Thyroid Function in Dogs" *JAVMA* 196:921–92 (1990).
Bakhshi, M.R. et al. Sequencing of the Primary Adhesion Domain of Bovine von Willebrand Factor: *Biochem. Biophys. Acta* 1132:325–28 (1992).
Benson, R.E. et al. "Efficiency and Precision of Electroimmunoassay for Canine Factor VIII–Related Antigen" *Am. J. Vet. Res.* 44:399–403 (1983).
Bergenhem, N.C.H. et al. "Mutation Creates an Open Reading Frame within the 5' Untranslated Region of Macaque Erythrocyte Carbonic Anhydrase (CA) I mRNA that Suppresses CA I Expression and Supports the Scanning Model for Translation" *Proc. Natl. Acad. Sci. USA* 89:8789–8802 (1992).
Bloom, A.L. "Von Willebrand Factor: Clinical Features of Inherited and Acquired Disorders" *Mayo Clin. Proc.* 66:743–51 (1991).
Bonthron, D. et al. "Nucleotide Sequence of Pre–Pro–von Willebrand Factor cDNA" *Nucleic Acids Res.* 14:7125–27 (1986).
Brinkhous, K.M. et al. "Pathophysiology of Platelet–Aggregating von Willebrand Factor: Applications of the Venom Coagglutinin vWF Assay" *Ann. New York Acad. Sci.* 370:191–204 (1981).
Brooks, M. "Clinical Features of Canine von Willebrand's Disease" *Proc. 9$^{th}$ ACVIM Forum*: 89–91 (1991).
Brooks, M. "Management of Canine von Willebrand's Disease" *Probl. In Vet. Med.* 4:636–46 (1992).
Brooks, M. et al. "Epidemiologic Features of von Willebrand's Disease in Doberman Pinschers, Scottish Terriers, and Shetland Sheepdogs: 260 Cases (1984–1988)" *JAVMA* 200:1123–27 (1992).
Dodds, W.J. "Von Willebrand's Disease in Dogs" *Mod. Vet. Pract.* 618–686 (1984).
Eikenboom, J. et al., "Dominant type 1 von Willebrand disease caused by mutated cysteine residues in the D3 domain of von Willebrand factor," *Blood*, Oct. 1, 1996;88(7):2433–41.
Ginsberg, D. et al. "Molecular Genetics of von Willebrand Disease" *Blood* 79:2507–19 (1992).
Holmes, N. et al., "Von Wille–brand's disease in UK dobermanns: possible correlation of a polymorphic DNA marker with disease status," *J. Small Anim. Pract.*, Jul. 1996;37(7):307–8.

(List continued on next page.)

*Primary Examiner*—Gary Benzion
*Assistant Examiner*—Joyce Tung
(74) *Attorney, Agent, or Firm*—Lahive & Cockfield, LLP; DeAnn F. Smith, Esq.

(57) ABSTRACT

The complete sequence of the canine von Willebrand Factor cDNA and deduced amino acid sequence is provided. The mutation which causes von Willebrand's Disease in Scottish Terriers, Doberman pinschers, Shetland sheepdogs, Manchester terriers and Poodles are also provided. Methods for detecting carriers of the defective vWF gene are also provided.

13 Claims, 18 Drawing Sheets

OTHER PUBLICATIONS

Janel, N. et al., "Comparison of the 5'–Flanking Sequences of the Human and Bovine von Willebrand Factor–Encoding Genes Reveals Alternation of Highly Homologous Domains with Species–Specific *Alu*–Type Repeats" *Gene* 167:291–95 (1995).

Johnson, G.S. et al. "A Bleeding Disease (von Willebrand's Disease) in a Chesapeake Bay Retriever" *JAVMA* 176:1261–63 (1980).

Johnson et al., "Canine von Willebrand's disease. A heterogeneous group of bleeding disorders," *Vet. Clin. North Am. Small Anim. Pract.*, Jan. 1988;18(1):195–229.

Kraus, K.H. et al. "Effect of Desmopressin Acetate on Bleeding Times and Plasma von Willebrand Factor in Doberman Pinscher Dogs with von Willebrand's Disease" *Vet. Surg.* 18:103–09 (1989).

Lankhof, H. et al. "Role of the Glycoprotein lb–Binding A1 Repeat and the RGD Sequence in Platelet Adhesion to Human Recombinant von Willebrand Factor" *Blood* 86:1035–42 (1995).

Lavergne, J.M. et al. "Primary Structure of the Factor VIII Binding Domain of Human, Porcine and Rabbit von Willebrand Factor" *Biochem. Biophys. Res. Commun.* 194:1019–24 (1993).

Mancuso, D.J. et al. "Human von Willebrand Factor Gene and Pseudogene: Structural Analysis and Differentiation by Polymerase Chain Reaction" *Biochemistry* 30:253–69 (1991).

Mancuso, D.J. et al. "1576 An Homologous Canine von Willebrand and Factor Binding Domain for Glycoprotein lb" *Thromb. Haemost.* 69:980 (1993).

Maniatis, T. et al. *Molecular Cloning: A Laboratory Manual*, Cold Spring Harbor Laboratory Press, Cold Spring, NY: 387–89 (1982).

Mansell, P.D. et al. "Changes in Factor VIII Activity and von Willebrand Factor Antigen Concentration with Age in Dogs" *Br. Vet. J.* 148:329–37 (1992).

Maquat, L. "Defects in RNA splicing and the consequence of shortened translational reading frames," *Am. J. Hum. Genet.*, Aug. 1996;59(2):279–86.

Meinkoth, J. et al., "Measurement of von Willebrand factor–specific mRNA and release and storage of von Willebrand factor from endothelial cells of dogs with type–l von Willebrand's disease," *Am. J. Vet. Res.*, Dec. 1995;56(12):1577–85.

Meyer, D. et al. "von Willebrand Factor: Structure and Function" *Thromb. Haemost.* 70:99–104 (1993).

Moser et al., "Temporal variation and factors affecting measurement of canine von Willebrand factor," *Am. J. Vet. Res.*, Sep. 1996;57(9):1288–93.

Nakai, K. et al., "Construction of a novel database containing aberrant splicing mutations of mammalian genes," *Gene*, Apr. 20, 1994; 141(2):171–7.

Nichols, W. et al., "von Willebrand disease in the RIIIS/J mouse is caused by a defect outside of the von Willebrand factor gene, *Blood*, Jun. 1, 1994;83(11):3225–31.

O'Brien, P.J. et al. "Use of a DNA–Based Test for the Mutation Associated with Porcine Stress Syndrome (Malignant Hyperthermia) in 10,000 Breeding Swine" *JAVMA* 203:842–51 (1993).

Panciera, D.L. et al. "Plasma von Willebrand Factor Antigen Concentration in Dogs with Hypothyroidism" *JAVMA* 205:1550–53 (1994).

Porter, C.A. et al. "Evidence of Mammalian Phylogeny from Sequences of Exon 28 of the von Willebrand Factor Gene" *Mol. Phylogenet. Evol.* 5:89–101 (1996).

Read, M.S. et al. "Venom Coagglutinin for Detection of von Willebrand Factor Activity in Animal Plasmas" *J. Lab. Clin. Med.* 101:74–82 (1983).

Richards, B. et al. "Multiplex PCR Amplification from the CFTR Gene Using DNA Prepared from Buccal Brushes/Swabs" *Human Molec. Genet.* 2:159–63 (1992).

Rosborough, T.K. et al. "Measurement of Canine von Willebrand Factor Using Ristocetin and Polybrene" *J. Lab. Clin. Med.* 96:47–56 (1980).

Rudolph, J.A. et al. "Periodic Paralysis in Quarter Horses: a Sodium Channel Mutation Disseminated by Selective Breeding" *Nat. Genet.* 2:144–47 (1992).

Ruggeri, Z.M. et al. "von Willebrand Factor" *FASEB J.* 7:308–16 (1993).

Sadler, J.E. et al. "Commentary: A New Classification for von Willebrand Disease" *Blood* 84:676–79 (1994).

Sambrook, J. et al. "Identification of cDNA Clones of Interest" *Molecular Cloning: A Laboratory Manual*, 2d Ed., vol. 2, Cold Spring Harbor Laboratory Press, Cold Spring, NY 8.46–8.47 (1989).

Shapiro, M. et al., "RNA splice junctions of different classes of eukaryotes: sequence statistics and functional implications in gene expression," *Nucleic Acids Res.* Sep. 11, 1987;15(17):7155–74.

Shibuya, H. et al. "A Polymorphic $(AGGATT)_n$ Tandem Repeat in an Intron of the Canine von Willebrand Factor Gene" *Anim. Genet.* 25:122 (1994).

Shuster, D.E. et al. "Identification and Prevalence of a Genetic Defect that Causes Leukocyte Adhesion Deficiency in Holstein Cattle" *Proc. Natl. Acad. Sci. USA* 89:9225–29 (1992).

Siguret, V. et al., "A novel case of compound heterozygosity with "Normandy"/type I von Willebrand disease (vWD). Direct demonstration of the segregation of one allele with a defective expression at the mRNA level causing type I vWD," *Hum. Genet.*, Feb. 1994;93(2):95–102.

Slappendel, R.J. "von Willebrand's Disease in Dutch Kooiker Dogs" *Vet–Q* 17:S21–S22 (1995).

Stirling, Y. et al. "Haemostasis in Normal Pregnancy" *Thromb. Haemost.* 52:176–82 (1984).

Stokol, T. et al. "Stability of von Willebrand Factor and Factor VIII in Canine Cryoprecipitate Under Various Conditions of Storage" *Res. Vet. Sci.* 59:152–55 (1995).

Stokol, T. et al. "von Willebrand's disease in Dobermann dogs in Australia," *Aust. Vet. J.*, Jul. 1995;72(7):257–62.

Strauss, H.S. et al. Elevation of Factor VIII (Antihemophilic Factor) During Pregnancy in Normal Persons and in a Patient with von Willebrand's Disease *New Eng. J. Med.* 269:1251–52 (1963).

Turrentine, M.A. et al. "Plasma from Donor Dogs, Pretreated with DDVAP, Transfused into German Shorthair Pointer with Type II von Willebrand's Disease" *Vet. Clin. North Am. Small Anim. Pract.* 18:275 (1988).

Venta, P.J. et al. "Gene–Specific Universal Mammalian Sequence–Tagged Sites: Application to the Canine Genome" *Biochem. Genet.* 34:321–41 (1996).

Verweij, C.L. et al. "Expression of Variant von Willebrand Factor (vWF) cDNA in Heterologous Cells: Requirement of the Pro–polypeptide in vWF Multimer Formation" *EMBO J.* 6:2885–90 (1987).

Wise, R.J. et al. "The Propeptide of von Willebrand Factor Independently Mediates the Assembly of von Willebrand Multimers" *Cell* 52:229–36 (1988).

\* cited by examiner

```
   1 CATTAANAGG TCCTGGCTGG GAGCTTTTTT TTGGGACCAG CACTCCATGT TCAAGGGCAA
  61 ACAGGGGCCA ATTAGGATCA ATCTTTTTTC TTTCTTTTTT TAAAAAAAAA AATTCTTCCC
 121 ACTTTGCACA CGGACAGTAG TACATACCAG TAGCTCTCTG CGAGGACGGT GATCACTAAT
 181 CATTTCTCCT GCTTCGTGGC AGATGAGTCC TACCAGACTT GTGAGGGTGC TGCTGGCTCT
 241 GGCCCTCATC TTGCCAGGGA AACTTTGTAC AAAAGGGACT GTTGGAAGGT CATCGATGGC
 301 CCGATGTAGC CTTCTCGGAG GTGACTTCAT CAACACCTTT GATGAGAGCA TGTACAGCTT
 361 TGCGGGAGAT TGCAGTTACC TCCTGGCTGG GGACTGCCAG GAACACTCCA TCTCACTTAT
 421 CGGGGGTTTC CAAAATGACA AAAGAGTGAG CCTCTCCGTG TATCTCGGAG AATTTTTCGA
 481 CATTCATTTG TTTGTCAATG GTACCATGCT GCAGGGGACC CAAAGCATCT CCATGCCCTA
 541 CGCCTCCAAT GGGCTGTATC TAGAGGCCGA GGCTGGCTAC TACAAGCTGT CCAGTGAGGC
 601 CTACGGCTTT GTGGCCAGAA TTGATGGCAA TGGCAACTTT CAAGTCCTGC TGTCAGACAG
 661 ATACTTCAAC AAGACCTGTG GGCTGTGTGG CAACTTTAAT ATCTTTGCTG AGGATGACTT
 721 CAAGACTCAA GAAGGGACGT TGACTTCGGA CCCCTATGAC TTTGCCAACT CCTGGGCCCT
 781 GAGCAGTGGG GAACAACGGT GCAAACGGGT GTCCCCTCCC AGCAGCCCAT GCAATGTCTC
 841 CTCTGATGAA GTGCAGCAGG TCCTGTGGGA GCAGTGCCAG CTCCTGAAGA GTGCCTCGGT
 901 GTTTGCCCGC TGCCACCCGC TGGTGGACCC TGAGCCTTTT GTCGCCCTGT GTGAAAGGAC
 961 TCTGTGCACC TGTGTCCAGG GGATGGAGTG CCCTTGTGCG GTCCTCCTGG AGTACGCCCG
1021 GGCCTGTGCC CAGCAGGGGA TTGTCTTGTA CGGCTGGACC GACCACAGCG TCTGCCGACC
1081 AGCATGCCCT GCTGGCATGG AGTACAAGGA GTGCGTGTCC CCTTGCACCA GAACTTGCCA
1141 GAGCCTTCAT GTCAAAGAAG TGTGTCAGGA GCAATGTGTA GATGGCTGCA GCTGCCCCGA
1201 GGGCCAGCTC CTGGATGAAG CCACTGCGT GGGAAGTGCT GAGTGTTCCT GTGTGCATGC
1261 TGGGCAACGG TACCCTCCGG GCGCCTCCCT CTTACAGGAC TGCCACACCT GCATTTGCCG
1321 AAATAGCCTG TGGATCTGCA GCAATGAAGA ATGCCCAGGC GAGTGTCTGG TCACAGGACA
1381 GTCCCACTTC AAGAGCTTCG ACAACAGGTA CTTCACCTTC AGTGGGGTCT GCCACTACCT
1441 GCTGGCCCAG GACTGCCAGG ACCACACATT CTCTGTTGTC ATAGAGACTG TCCAGTGTGC
1501 CGATGACCTG GATGCTGTCT GCACCCGCTC GGTCACCGTC CGCCTGCCTG ACATCACAA
1561 CAGCCTTGTG AAGCTGAAGA ATGGGGGAGG AGTCTCCATG GATGGCCAGG ATATCCAGAT
1621 TCCTCTCCTG CAAGGTGACC TCCGCATCCA GCACACCGTG ATGGCCTCCG TGCGCCTCAG
1681 CTACGGGGAG GACCTGCAGA TGGATTCGGA CGTCCGGGGC AGGCTACTGG TGACGCTGTA
1741 CCCCGCCTAC GCGGGGAAGA CGTGCGGCCG TGGCGGGAAC TACAACGGCA ACCGGGGGGA
1801 CGACTTCGTG ACGCCCGCAG GCCTGGCGGA GCCCCTGGTG GAGGACTTCG GGAACGCCTG
1861 GAAGCTGCTC GGGGCCTGCG AGAACCTGCA GAAGCAGCAC CGCGATCCCT GCAGCCTCAA
1921 CCCGCGCCAG GCCAGGTTTG CGGAGGAGGC GTGCGCGCTG CTGACGTCCT CGAAGTTCGA
1981 GCCCTGCCAC CGAGCGGTGG GTCCTCAGCC CTACGTGCAG AACTGCCTCT ACGACGTCTG
2041 CTCCTGCTCC GACGGCAGAG ACTGTCTTTG CAGCGCCGTG GCCAACTACG CCGCAGCCGT
2101 GGCCCGGAGG GGCGTGCACA TCGCGTGGCG GGAGCCGGGC TTCTGTGCGC TGAGCTGCCC
2161 CCAGGGCCAG GTGTACCTGC AGTGTGGGAC CCCCTGCAAC ATGACCTGTC TCTCCCTCTC
2221 TTACCCGGAG GAGGACTGCA ATGAGGTCTG CTTGGAAAGC TGCTTCTCCC CCCAGGGCT
2281 GTACCTGGAT GAGAGGGGAG ATTGTGTGCC CAAGGCTCAG TGTCCCTGTT ACTATGATGG
2341 TGAGATCTTT CAGCCCGAAG ACATCTTCTC AGACCATCAC ACCATGTGCT ACTGTGAGGA
2401 TGGCTTCATG CACTGTACCA CAAGTGGAGG CCTGGGAAGC CTGCTGCCCA ACCCGGTGCT
2461 CAGCAGCCCC CGGTGTCACC GCAGCAAAAG GAGCCTGTCC TGTCGGCCCC CCATGGTCAA
2521 GTTGGTGTGT CCCGCTGATA ACCCGAGGGC TGAAGGACTG GAGTGTGCCA AAACCTGCCA
2581 GAACTATGAC CTGCAGTGCA TGAGCACAGG CTGTGTCTCC GGCTGCCTCT GCCCGCAGGG
```

*Fig. 1A*

```
2641 CATGGTCCGG CATGAAAACA GGTGTGTGGC GCTGGAAAGA TGTCCCTGCT TCCACCAAGG
2701 CCAAGAGTAC GCCCCAGGAG AAACCGTGAA AATTGACTGC AACACTTGTG TCTGTCGGGA
2761 CCGGAAGTGG ACCTGCACAG ACCATGTGTG TGATGCCACT TGCTCTGCCA TCGGCATGGC
2821 GCACTACCTC ACCTTCGACG GACTCAAGTA CCTGTTCCCT GGGGAGTGCC AGTATGTTCT
2881 GGTGCAGGAT TACTGCGGCA GTAACCCTGG GACCTTACGG ATCCTGGTGG GGAACGAGGG
2941 GTGCAGCTAC CCCTCAGTGA AATGCAAGAA GCGGGTCACC ATCCTGGTGG AAGGAGGAGA
3001 GATTGAACTG TTTGATGGGG AGGTGAATGT GAAGAAACCC ATGAAGGATG AGACTCACTT
3061 TGAGGTGGTA GAGTCTGGTC AGTACGTCAT TCTGCTGCTG GGCAAGGCAC TCTCTGTGGT
3121 CTGGGACCAC CGCCTGAGCA TCTCTGTGAC CCTGAAGCGG ACATACCAGG AGCAGGTGTG
3181 TGGCCTGTGT GGGAATTTTG ATGGCATCCA GAACAATGAT TTCACCAGCA GCAGCCTCCA
3241 AATAGAAGAA GACCCTGTGG ACTTTGGGAA TTCCTGGAAA GTGAACCCGC AGTGTGCCGA
3301 CACCAAGAAA GTACCACTGG ACTCATCCCC TGCCGTCTGC CACAACAACA TCATGAAGCA
3361 GACGATGGTG GATTCCTCCT GCAGGATCCT CACCAGTGAT ATTTTCCAGG ACTGCAACAG
3421 GCTGGTGGAC CCTGAGCCAT TCCTGGACAT TTGCATCTAC GACACTTGCT CCTGTGAGTC
3481 CATTGGGGAC TGCACCTGCT TCTGTGACAC CATTGCTGCT TACGCCCACG TCTGTGCCCA
3541 GCATGGCAAG GTGGTAGCCT GGAGGACAGC CACATTCTGT CCCCAGAATT GCGAGGAGCG
3601 GAATCTCCAC GAGAATGGGT ATGAGTGTGA GTGGCGCTAT AACAGCTGTG CCCCTGCCTG
3661 TCCCATCACG TGCCAGCACC CCGAGCCACT GGCATGCCCT GTACAGTGTG TTGAAGGTTG
3721 CCATGCGCAC TGCCCTCCAG GGAAAATCCT GGATGAGCTT TTGCAGACCT GCATCGACCC
3781 TGAAGACTGT CCTGTGTGTG AGGTGGCTGG TCGTCGCTTG GCCCCAGGAA AGAAAATCAT
3841 CTTGAACCCC AGTGACCCTG AGCACTGCCA AATTTGTAAT TGTGATGGTG TCAACTTCAC
3901 CTGTAAGGCC TGCAGAGAAC CCGGAAGTGT TGTGGTGCCC CCCACAGATG GCCCCATTGG
3961 CTCTACCACC TCGTATGTGG AGGACACGTC GGAGCCGCTC CTCCATGACT TCCACTGCAG
4021 CAGGCTTCTG GACCTGGTTT TCCTGCTGGA TGGCTCCTCC AAGCTGTCTG AGGACGAGTT
4081 TGAAGTGCTG AAGGTCTTTG TGGTGGGTAT GATGGAGCAT CTGCACATCT CCCAGAAGCG
4141 GATCCGCGTG GCTGTGGTGG AGTACCACGA CGGCTCCCAC GCCTACATCG AGCTCAAGGA
4201 CCGGAAGCGA CCCTCAGAGC TGCGGCGCAT CACCAGCCAG GTGAAGTACG CGGGCAGCGA
4261 GGTGGCCTCC ACCAGTGAGG TCTTAAAGTA CACGCTGTTC CAGATCTTTG GCAAGATCGA
4321 CCGCCCGGAA GCGTCTCGCA TTGCCCTGCT CCTGATGGCC AGCCAGGAGC CCTCAAGGCT
4381 GGCCCGGAAT TTGGTCCGCT ATGTGCAGGG CCTGAAGAAG AAGAAAGTCA TTGTCATCCC
4441 TGTGGGCATC GGGCCCCACG CCAGCCTTAA GCAGATCCAC CTCATAGAGA AGCAGGCCCC
4501 TGAGAACAAG GCCTTTGTGT TCAGTGGTGT GGATGAGTTG GAGCAGCGAA GGGATGAGAT
4561 TATCAACTAC CTCTGTGACC TTGCCCCCGA AGCACCTGCC CCTACTCAGC ACCCCCCAAT
4621 GGCCCAGGTC ACGGTGGGTT CGGAGCTGTT GGGGGTTTCA TCTCCAGGAC CAAAAGGAA
4681 CTCCATGGTC CTGGATGTGG TGTTTGTCCT GGAAGGGTCA GACAAAATTG GTGAGGCCAA
4741 CTTTAACAAA AGCAGGGAGT TCATGGAGGA GGTGATTCAG CGGATGGACG TGGGCCAGGA
4801 CAGGATCCAC GTCACAGTGC TGCAGTACTC GTACATGGTG ACCGTGGAGT ACACCTTCAG
4861 CGAGGCGCAG TCCAAGGGCG AGGTCCTACA GCAGGTGCGG GATATCCGAT ACCGGGGTGG
4921 CAACAGGACC AACACTGGAC TGGCCCTGCA ATACCTGTCC GAACACAGCT TCTCGGTCAG
4981 CCAGGGGGAC CGGGAGCAGG TACCTAACCT GGTCTACATG GTCACAGGAA ACCCCGCTTC
5041 TGATGAGATC AAGCGGATGC CTGGAGACAT CCAGGTGGTG CCCATCGGGG TGGGTCCACA
5101 TGCCAATGTG CAGGAGCTGG AGAAGATTGG CTGGCCCAAT GCCCCCATCC TCATCCATGA
5161 CTTTGAGATG CTCCCTCGAG AGGCTCCTGA TCTGGTGCTA CAGAGGTGCT GCTCTGGAGA
5221 GGGGCTGCAG ATCCCCACCC TCTCCCCCAC CCCAGATTGC AGCCAGCCCC TGGATGTGGT
5281 CCTCCTCCTG GATGGCTCTT CCAGCATTCC AGCTTCTTAC TTTGATGAAA TGAAGAGCTT
```

*Fig. 1B*

```
5341 CACCAAGGCT TTTATTTCAA GAGCTAATAT AGGGCCCCGG CTCACTCAAG TGTCGGTGCT
5401 GCAATATGGA AGCATCACCA CTATCGATGT GCCTTGGAAT GTAGCCTATG AGAAAGTCCA
5461 TTTACTGAGC CTTGTGGACC TCATGCAGCA GGAGGGAGGC CCCAGCGAAA TTGGGGATGC
5521 TTTGAGCTTT GCCGTGCGAT ATGTCACCTC AGAAGTCCAT GGTGCCAGGC CCGGAGCCTC
5581 GAAAGCGGTG GTTATCCTAG TCACAGATGT CTCCGTGGAT TCAGTGGATG CTGCAGCCGA
5641 GGCCGCCAGA TCCAACCGAG TGACAGTGTT CCCCATTGGA ATCGGGGATC GGTACAGTGA
5701 GGCCCAGCTG AGCAGCTTGG CAGGCCCAAA GGCTGGCTCC AATATGGTAA GGCTCCAGCG
5761 AATTGAAGAC CTCCCCACCG TGGCCACCCT GGGAAATTCC TTCTTCCACA AGCTGTGCTC
5821 TGGGTTTGAT AGAGTTTGCG TGGATGAGGA TGGGAATGAG AAGAGGCCCG GGGATGTCTG
5881 GACCTTGCCA GACCAGTGCC ACACAGTGAC TTGCCTGCCA GATGGCCAGA CCTTGCTGAA
5941 GAGTCATCGG GTCAACTGTG ACCGGGGGCC AAGGCCTTCG TGCCCCAATG GCCAGCCCCC
6001 TCTCAGGGTA GAGGAGACCT GTGGCTGCCG CTGGACCTGT CCCTGTGTGT GCATGGGCAG
6061 CTCTACCCGG CACATCGTGA CCTTTGATGG GCAGAATTTC AAGCTGACTG GCAGCTGTTC
6121 GTATGTCCTA TTTCAAAACA AGGAGCAGGA CCTGGAGGTG ATTCTCCAGA ATGGTGCCTG
6181 CAGCCCTGGG GCGAAGGAGA CCTGCATGAA ATCCATTGAG GTGAAGCATG ACGGCCTCTC
6241 AGTTGAGCTC CACAGTGACA TGCAGATGAC AGTGAATGGG AGACTAGTCT CCATCCCATA
6301 TGTGGGTGGA GACATGGAAG TCAATGTTTA TGGGACCATC ATGTATGAGG TCAGATTCAA
6361 CCATCTTGGC CACATCTTCA CATTCACCCC CCAAAACAAT GAGTTCCAGC TGCAGCTCAG
6421 CCCCAGGACC TTTGCTTCGA AGACATATGG TCTCTGTGGG ATCTGTGATG AGAACGGAGC
6481 CAATGACTTC ATTCTGAGGG ATGGGACAGT CACCACAGAC TGGAAGGCAC TCATCCAGGA
6541 ATGGACCGTA CAGCAGCTTG GGAAGACATC CCAGCCTGTC CATGAGGAGC AGTGTCCTGT
6601 CTCCGAATTC TTCCACTGCC AGGTCCTCCT CTCAGAATTG TTTGCCGAGT GCCACAAGGT
6661 CCTCGCTCCA GCCACCTTTT ATGCCATGTG CCAGCCCGAC AGTTGCCACC CGAAGAAAGT
6721 GTGTGAGGCG ATTGCCTTGT ATGCCCACCT CTGTCGGACC AAAGGGGTCT GTGTGGACTG
6781 GAGGAGGGCC AATTTCTGTG CTATGTCATG TCCACCATCC CTGGTGTACA ACCACTGTGA
6841 GCATGGCTGC CCTCGGCTCT GTGAAGGCAA TACAAGCTCC TGTGGGGACC AACCCTCGGA
6901 AGGCTGCTTC TGCCCCCCAA ACCAAGTCAT GCTGGAAGGT AGCTGTGTCC CCGAGGAGGC
6961 CTGTACCCAG TGCATCAGCG AGGATGGAGT CCGGCACCAG TTCCTGGAAA CCTGGGTCCC
7021 AGCCCACCAG CCTTGCCAGA TCTGCACGTG CCTCAGTGGG CGGAAGGTCA ACTGTACGTT
7081 GCAGCCCTGC CCCACAGCCA AAGCTCCCAC CTGTGGCCCG TGTGAAGTGG CCCGCCTCCG
7141 CCAGAACGCA GTGCAGTGCT GCCCGGAGTA CGAGTGTGTG TGTGACCTGG TGAGCTGTGA
7201 CCTGCCCCCG GTGCCTCCCT GCGAAGATGG CCTCCAGATG ACCCTGACCA ATCCTGGCGA
7261 GTGCAGACCC AACTTCACCT GTGCCTGCAG GAAGGATGAA TGCAGACGGG AGTCCCCGCC
7321 CTCTTGTCCC CCGCACCGGA CGCCGGCCCT TCGGAAGACT CAGTGCTGTG ATGAGTATGA
7381 GTGTGCATGC AACTGTGTCA ACTCCACGGT GAGCTGCCCG CTTGGGTACC TGGCCTCGGC
7441 TGTCACCAAC GACTGTGGCT GCACCACAAC AACCTGCTTC CCTGACAAGG TGTGTGTCCA
7501 CCGAGGCACC ATCTACCCTG TGGGCCAGTT CTGGGAGGAG GCCTGTGACG TGTGCACCTG
7561 CACGGACTTG GAGGACTCTG TGATGGGCCT GCGTGTGGCC CAGTGCTCCC AGAAGCCCTG
7621 TGAGGACAAC TGCCTGTCAG GCTTCACTTA TGTCCTTCAT GAAGGCGAGT GCTGTGGAAG
7681 GTGTCTGCCA TCTGCCTGTG AGGTGGTCAC TGGTTCACCA CGGGGCGACG CCCAGTCTCA
7741 CTGGAAGAAT GTTGGCTCTC ACTGGGCCTC CCCTGACAAC CCCTGCCTCA TCAATGAGTG
7801 TGTCCGAGTG AAGGAAGAGG TCTTTGTGCA ACAGAGGAAT GTCTCCTGCC CCAGCTGAA
7861 TGTCCCCACC TGCCCCACGG GCTTCCAGCT GAGCTGTAAG ACCTCAGAGT GTTGTCCCAC
7921 CTGTCACTGC GAGCCCCTGG AGGCCTGCTT GCTCAATGGT ACCATCATTG GGCCGGGGAA
7981 AAGTCTGATG ATTGATGTGT GTACAACCTG CCGCTGCACC GTGCCGGTGG GAGTCATCTC
```

*Fig. 1C*

```
8041 TGGATTCAAG CTGGAGGGCA GGAAGACCAC CTGTGAGGCA TGCCCCCTGG GTTATAAGGA
8101 AGAGAAGAAC CAAGGTGAAT GCTGTGGGAG ATGTCTGCCT ATAGCTTGCA CCATTCAGCT
8161 AAGAGGAGGA CAGATCATGA CACTGAAGCG TGATGAGACT ATCCAGGATG GCTGTGACAG
8221 TCACTTCTGC AAGGTCAATG AAAGAGGAGA GTACATCTGG GAGAAGAGAG TCACGGGTTG
8281 CCCACCTTTC GATGAACACA AGTGTCTGGC TGAGGGAGGA AAAATCATGA AAATTCCAGG
8341 CACCTGCTGT GACACATGTG AGGAGCCAGA ATGCAAGGAT ATCATTGCCA AGCTGCAGCG
8401 TGTCAAAGTG GGAGACTGTA AGTCTGAAGA GGAAGTGGAC ATTCATTACT GTGAGGGTAA
8461 ATGTGCCAGC AAAGCCGTGT ACTCCATCCA CATGGAGGAT GTGCAGGACC AGTGCTCCTG
8521 CTGCTCGCCC ACCCAGACGG AGCCCATGCA GGTGGCCCTG CGCTGCACCA ATGGCTCCCT
8581 CATCTACCAT GAGATCCTCA ATGCCATCGA ATGCAGGTGT TCCCCAGGA AGTGCAGCAA
8641 GTGAGGCCAC TGCCTGGATG CTACTGTCGC CTGCCTTACC CGACCTCACT GGACTGGCCA
8701 GAGTGCTGCT CAGTCCTCCT CAGTCCTCCT CCTGCTCTGC TCTTGTGCTT CCTGATCCCA
8761 CAATAAAGGT CAATCTTTCA CCTTGAAAAA AAAAAAAAA AA
```

*Fig. 1D*

| | | |
|---|---|---|
| Human | MIPARFAGVLLALALILPGTLCAEGTRGRSSTARCSLFGSDFVNTFDGSMYSFAGYCSYL | 60 |
| Dog | -S-T-LVR----------K--TK--V----M-----L-G--I----E-------D--- | |
| | * | |
| Human | LAGGCQKRSFSIIGDFQNGKRVSLSVYLGEFFDIHLFVNGTVTQGDQRVSMPYASKGLYL | 120 |
| Dog | ---D--EH-I-L--G---D------------------ML--T-SI------N---- | |
| Human | ETEAGYYKLSGEAYGFVARIDGSGNFQVLLSDRYFNKCTCGLCGNFNIFAEDDFMTQEGTL | 180 |
| Dog | -A--------S-----------N---------------------K------ | |
| Human | TSDPYDFANSWALSSGEQWCERASPPSSSCNISSGEMQKGLWEQCQLLKSTSVFARCHPL | 240 |
| Dog | ------------------R-K-V-----P--V--D-V-QV---------A-------- | |
| Human | VDPEPFVALCEKTLCECAGGLECACPALLEYARTCAQEGMVLYGWTDHSACSPVCPAGME | 300 |
| Dog | ------------R---T-VQ-M--P-AV------A---Q-I---------V-R-A------ | |
| Human | YRQCVSPCARTCQSLHINEMCQERCVDGCSCPEGQLLDEGLCVESTECPCVHSGKRYPPG | 360 |
| Dog | -KE-----T-------VK-V---Q----------------H--G-A--S---A-Q----- | |
| Human | TSLSRDCNTCICRNSQWICSNEECPGECLVTGQSHFKSFDNRYFTFSGICQYLLARDCQD | 420 |
| Dog | A--LQ--H-------L--------------------------V-H----Q--- | |
| Human | HSFSIVIETVQCADDRDAVCTRSVTVRLPGLHNSLVKLKHGAGVAMDGQDVQLPLLKGDL | 480 |
| Dog | -T--V----------L-------------H--------N-G--S-----I-I---Q--- | |
| Human | RIQHTVTASVRLSYGEDLQMDWDGRGRLLVKLSPVYAGKTCGLCGNYNGNQGDDFLTPSG | 540 |
| Dog | ------M---------------S-V------T-Y-A--------RG------R----V--A- | |
| Human | LAEPRVEDFGNAWKLHGDCQDLQKQHSDPCALNPRMTRFSEEACAVLTSPTFEACHRAVS | 600 |
| Dog | ----L----------L-A-EN-----R---S----QA--A-----L---SK--P-----G | |
| Human | PLPYLRNCRYDVCSCSDGRECLCGALASYAAACAGRGVRVAWREPGRCELNCPKGQVYLQ | 660 |
| Dog | -Q--VQ--L---------D---S-V-N----V-R---HI------F-A-S--Q------ | |
| Human | CGTPCNLTCRSLSYPDEECNEACLEGCFCPPGLYMDERGDCVPKAQCPCYYDGEIFQPED | 720 |
| Dog | ------M--L-----E-D---V---S--S-----L---------------- | |
| Human | IFSDHHTMCYCEDGFMHCTMSGVPGSLLPDAVLSSPLSHRSKRSLSCRPPMVKLVCPADN | 780 |
| Dog | -----------------T--GL-----NP-----RC---------------------- | |
| Human | LRAEGLECTKTCQNYDLECMSMGCVSGCLCPPGMVRHENRCVALERCPCFHQGKEYAPGE | 840 |
| Dog | P-------A---------Q---T--------Q------------------Q------ | |
| Human | TVKIGCNTCVCRDRKWNCTDHVCDATCSTIGMAHYLTFDGLKYLFPGECQYVLVQDYCGS | 900 |
| Dog | ----D-------T----------A---------------------------- | |

*Fig. 2A*

| | | |
|---|---|---|
| Human | NPGTFRILVGNKGCSHPSVKCKKRVTILVEGGEIELFDGEVNVKRPMKDETHFEVVESGR | 960 |
| Dog | ----L------E---Y--------------------------K------------Q | |
| | | |
| Human | YIILLLGKALSVVWDRHLSISVVLKQTYQEKVCGLCGNFDGIQNNDLTSSNLQVEEDPVD | 1020 |
| Dog | -V-----------HR-----T--R---Q--------------F---S--I------ | |
| | | |
| Human | FGNSWKVSSQCADTRKVPLDSSPATCHNNIMKQTMVDSSCRILTSDVFQDCNKLVDPEPY | 1080 |
| Dog | -------NP-----K---------V--------------------I-----R------F | |
| | | |
| Human | LDVCIYDTCSCESIGDCACFCDTIAAYAHVCAQHGKVVTWRTATLCPQSCEERNLRENGY | 1140 |
| Dog | --I------------T--------------------A-----F---N------H---- | |
| | | |
| Human | ECEWRYNSCAPACQVTCQHPEPLACPVQCVEGCHAHCPPGKILDELLQTCVDPEDCPVCE | 1200 |
| Dog | ---------------PI-----------------------------I--------- | |
| | | |
| Human | VAGRRFASGKKVTLNPSDPEHCQICHCDVVNLTCEACQEPGGLVVPPTDAPVSPTTLYVE | 1260 |
| Dog | -----L-P---II------------N--G--F--K--R---SV------G-IGS--S--- | |
| | | |
| Human | DISEPPLHDFYCSRLLDLVFLLDGSSRLSEAEFEVLKAFVVDMMERLRISQKWVRVAVVE | 1320 |
| Dog | -T--------H---------------K---D------V---G---H-H---RI------ | |
| | | |
| Human | YHDGSHAYIGLKDRKRPSELRRIASQVKYAGSQVASTSEVLKYTLFQIFSKIDRPEASRI | 1380 |
| Dog | ---------E-------------T--------E-----------------G---------- | |
| | | |
| Human | ALLLMASQEPQRMSRNFVRYVQGLKKKKVIVIPVGIGPHANLKQIRLIEKQAPENKAFVL | 1440 |
| Dog | -----------S-IA--L-------------------S----H------------F | |
| | | |
| Human | SSVDELEQQRDEIVSYLCDLAPEAPPPTLPPHMAQVTVGPGLLGVSTLGPKRNSMVLDVA | 1500 |
| Dog | -G------R----IN----------A--QH-P-------SE-----SP----------V | |
| | | |
| Human | FVLEGSDKIGEADFNRSKEFMEEVIQRMDVGQDSIHVTVLQYSYMVTVEYPFSEAQSKGD | 1560 |
| Dog | -------------N--K-R--------------R----------------T--------E | |
| | | |
| Human | ILQRVREIRYQGGNRINTGLALRYLSDHSFLVSQGDREQAPNLVYMVTGNPASDEIKRLP | 1620 |
| Dog | V--Q--D---R----------Q---E---S--------V-----------------M- | |
| | | |
| Human | GDIQVVPIGVGPNANVQELERIGWPNAPILIQDFETLPREAPDLVLQRCCSGEGLQIPTL | 1680 |
| Dog | -------------H-------K---------H---M-------------------- | |
| | | |
| Human | SPAPDCSQPLDVILLLDGSSSFPASYFDEMKSFAKAFISKANIGPRLTQVSVLQYGSITT | 1740 |
| Dog | --T----------V---------I----------T-----R----------------- | |
| | | |
| Human | IDVPWNVVPEKAHLLSLVDVMQREGGPSQIGDALGFAVRYLTSEMHGARPGASKAVVILV | 1800 |
| Dog | -------AY--V--------L--Q-----E-----S-----V---V------------ | |

*Fig. 2B*

| | | |
|---|---|---|
| Human | TDVSVDSVDAAADAARSNRVTVFPIGIGDRYDAAQLRILAGPAGDSNVVKLQRIEDLPTM | 1860 |
| Dog | ------------E----------------SE---SS----KAG--M-R---------V | |
| Human | VTLGNSFLHKLCSGFVRICMDEDGNEKRPGDVWTLPDQCHTVTCQPDGQTLLKTHRVNCD | 1920 |
| Dog | A------F-------D-V-V---------------------L--------S------ | |
| Human | RGLRPSCPNSQSPVKVEETCGCRWTCPCVCTGSSTRHIVTFDGQNFKLTGSCSYVLFQNK | 1980 |
| Dog | --P-------G-P-LR--------------M--------------------------- | |
| Human | EQDLEVILHNGACSPGARQGCMKSIEVKHSALSVELHSDMEVTVNGRLVSVPYVGGNMEV | 2040 |
| Dog | --------Q---------KET--------DG---------QM---------I-----D--- | |
| Human | NVYGAIMHEVRFNHLGHIFTFTPQNNEFQLQLSPKTFASKTYGLCGICDENGANDFMLRD | 2100 |
| Dog | ----T--Y----------------------R---------------------I--- | |
| Human | GTVTTDWKTLVQEWTVQRPGQTCQPILEEQCLVPDSSHCQVLLLPLFAECHKVLAPATFY | 2160 |
| Dog | --------A-I------QL-K-S--VH----P-SEFF-------SE------------- | |
| Human | AICQQDSCHQEQVCEVIASYAHLCRTNGVCVDWRTPDFCAMSCPPSLVYNHCEHGCPRHC | 2220 |
| Dog | -M--P----PKK---A--L-------K------RAN--------------------L- | |
| Human | DGNVSSCGDHPSEGCFCPPDKVMLEGSCVPEEACTQCIGEDGVQHQFLEAWVPDHQPCQI | 2280 |
| Dog | E--T-----Q--------NQ----------------S----R-----T---A------ | |
| Human | CTCLSGRKVNCTTQPCPTAKAPTCGLCEVARLRQNADQCCPEYECVCDPVSCDLPPVPHC | 2340 |
| Dog | -------------L-----------P----------V-----------L--------P- | |
| Human | ERGLQPTLTNPGECRPNFTCACRKEECKRVSPPSCPPHRLPTLRKTQCCDEYECACNCVN | 2400 |
| Dog | -D---M-------------D--R-E--------T-A------------------ | |
| Human | STVSCPLGYLASTATNDCGCTTTTCLPDKVCVHRSTIYPVGQFWEEGCDVCTCTDMEDAV | 2460 |
| Dog | -------------AV--------F--------G-----------A-------L--S- | |
| Human | MGLRVAQCSQKPCEDSCRSGFTYVLHEGECCGRCLPSACEVVTGSPRGDSQSSWKSVGSQ | 2520 |
| Dog | ---------------N-L-----------------------------A--H--N---H | |
| Human | WASPENPCLINECVRVKEEVFIQQRNVSCPQLEVPVCPSGFQLSCKTSACCPSCRCERME | 2580 |
| Dog | ----D--------------V---------N--T--T---------E---T-H--PL- | |
| Human | ACMLNGTVIGPGKTVMIDVCTTCRCMVQVGVISGFKLECRKTTCNPCPLGYKEENNTGEC | 2640 |
| Dog | --L----I-----SL---------T-P----------G-----EA--------K-Q--- | |
| Human | CGRCLPTACTIQLRGGQIMTLKRDETLQDGCDTHFCKVNERGEYFWEKRVTGCPPFDEHK | 2700 |
| Dog | ------I-----------I-----S-----------I-------------- | |

Fig. 2C

```
Human  CLAEGGKIMKIPGTCCDTCEEPECNDITARLQYVKVGSCKSEVEVDIHYCQGKCASKAMY    2760
Dog    -------------------K--I-K--R----D----E-------E-------V-

Human  SIDINDVQDQCSCCSPTRTEPMQVALHCTNGSVVYHEVLNAMECKCSPRKCSK          2813
Dog    --HME----------Q--------R-----LI---I---I--R-------
```

*Fig. 2D* exon 4       AAATGACAAAAGAGTGAGCCGGTC*
AGGGGGTTTCCAAAATGACAAAAGAGTGAGCCTCTCCGTGTATCTCGGAGAATTTTTCGA
   G  G  F  Q  N  D  K  R  V  S  L  S  V  Y  L  G  E  F  F  D CATTCATTTGTTTGTCAATGGTACCATGCTGCAGGGGACCCAAAGGTAAGTCAGAAGCCC
   I  H  L  F  V  N  G  T  M  L  Q  G  T  Q  R

GAATGTTCAGGTTAATATGGACCCTGGGGATCACTTTGCAACCCCCTTGTTTTTTCAGAT

GAGGGAGCCGGGGCCCAGAGACAGGAAGTAAATGTGCCCAGGGAAAGTGAGTGGCAGGAC

TGGGTGAAAGCCCCATATCCCGACTCCTGGTCAAGGAGACTTTGCACCAAGGTCCCAGCC
                   3'-GGGCTGGCGACCAGTTCCTCTGAA-5'

CTGGAGCATGGGGTTGGGGTTGGAAGGTGGAGGGACATGGAGGAAATGCATGAGAAGCAC
                          exon 5
GCTTCCTGAGCTCCTCCTTGTCCCACCAGCATCTCCATGCCCTACGCCTCCAATGGGC
                         I  S  M  P  Y  A  S  N  G

*Fig. 4*

Normal Allele

Exon 43                    Intron 43          Exon 44
                              *
AGGACAACTGCCTGCCTGTCGgtgagtggggg ... GGCTTCACTTAT
                |||||||
            AGGTRAGT    Donor Consensus

Mutant Allele
                              *
AGGACAACTGCCTGCCTgtcagtgagtggggg ... GGCTTCACTTAT
                || |||
            AGGTRAGT    Donor Consensus

*Fig. 6*

Exon 7

```
       V   L   W   E   Q   C   Q   L   L   K   S   A   S   V   F   A   R   C   H   P   L   V
       GTCCTGTGGGAGCAGTGCCAGCTCCTGAAGAGTGCCTCGGTGTTTGCCCGCTGCCACCCGCTGGTG
        TCCTGTGGGAGCAGTGCCAG
       DVWFEX7D     GCNNNNNNNGC  Mwo I

D   P   E   P   F   V   A   L   C   E   R   T   L   C   T   C   V   Q   G   M   E   C
       GACCCTGAGCCTTTTGTCGCCCTGTGTGAAAGGACTCTGTGCACCTGTGTCCAGGGGATGGAGTGC
                GCNNNN-NNNGC   Mwo I
                    735

P   C   A   V   L   L   E   Y   A   R   A   C   A   Q   Q   G   I   V   L   Y   G   W
       CCTTGTGCGGTCCTCCTGGAGTACGCCCGGGCCTGTGCCCAGCAGGGAATTGTGCTGTACGGCTGG
                                                                  ATGCCGACC

T   D   H   S   V   C   R
       ACCGACCACAGCGTCTGCCG
       TGGCTGGTG-5'
       DVWFEX7U
```

*Fig. 11*

SEQUENCE LISTING

<160> NUMBER OF SEQ ID NOS: 29

<210> SEQ ID NO 1
<211> LENGTH: 8802
<212> TYPE: DNA
<213> ORGANISM: Canis familiaris

<400> SEQUENCE: 1
cattaaaagg tcctggctgg gagcttttt ttgggaccag cactccatgt tcaagggcaa     60 acagggcca attaggatca atcttttttc tttctttttt taaaaaaaaa aattcttccc    120

```
actttgcaca cggacagtag tacataccag tagctctctg cgaggacggt gatcactaat    180
catttctcct gcttcgtggc agatgagtcc taccagactt gtgagggtgc tgctggctct    240
ggccctcatc ttgccaggga aactttgtac aaaagggact gttggaaggt catcgatggc    300
ccgatgtagc cttctcggag gtgacttcat caacaccttt gatgagagca tgtacagctt    360
tgcgggagat tgcagttacc tcctggctgg ggactgccag gaacactcca tctcacttat    420
cgggggtttc caaaatgaca aaagagtgag cctctccgtg tatctcggag aattttcga    480 cattcatttg tttgtcaatg gtaccatgct gcagggacc caaagcatct ccatgcccta    540
cgcctccaat gggctgtatc tagaggccga ggctggctac tacaagctgt ccagtgaggc    600
ctacggcttt gtggccagaa ttgatggcaa tggcaacttt caagtcctgc tgtcagacag    660
atacttcaac aagacctgtg ggctgtgtgg caactttaat atctttgctg aggatgactt    720
caagactcaa gaagggacgt tgacttcgga ccctatgac tttgccaact cctgggccct    780
gagcagtggg gaacaacggt gcaaacgggt gtcccctccc agcagcccat gcaatgtctc    840
ctctgatgaa gtgcagcagg tcctgtggga gcagtgccag ctcctgaaga gtgcctcggt    900
gtttgcccgc tgccacccgc tggtggaccc tgagcctttt gtcgccctgt gtgaaaggac    960
tctgtgcacc tgtgtccagg ggatggagtg cccttgtgcg gtcctcctgg agtacgcccg   1020
ggcctgtgcc cagcagggga ttgtcttgta cggctggacc gaccacagcg tctgccgacc   1080
agcatgccct gctggcatgg agtacaagga gtgcgtgtcc ccttgcacca gaacttgcca   1140
gagccttcat gtcaaagaag tgtgtcagga gcaatgtgta gatggctgca gctgccccga   1200
gggccagctc ctggatgaag gccactgcgt gggaagtgct gagtgttcct gtgtgcatgc   1260
tgggcaacgg taccctccgg gcgcctccct cttacaggac tgccacacct gcatttgccg   1320
aaatagcctg tggatctgca gcaatgaaga atgcccaggc gagtgtctgg tcacaggaca   1380 gtccccacttc aagagcttcg acaacaggta cttcaccttc agtggggtct gccactacct   1440
gctggcccag gactgccagg accacacatt ctctgttgtc atagagactg tccagtgtgc   1500
cgatgacctg gatgctgtct gcacccgctc ggtcaccgtc cgcctgcctg acatcacaa    1560 cagccttgtg aagctgaaga atgggggagg agtctccatg gatggccagg atatccagat   1620
tcctctcctg caaggtgacc tccgcatcca gcacaccgtg atggcctccg tgcgcctcag   1680 ctacgggag gacctgcaga tggattcgga cgtccggggc aggctactgg tgacgctgta   1740
ccccgcctac gcggggaaga cgtgcggccg tggcgggaac tacaacggca accggggga    1800 cgacttcgtg acgcccgcag gcctggcgga gcccctggtg gaggacttcg ggaacgcctg   1860
gaagctgctc ggggcctgcg agaacctgca gaagcagcac cgcgatccct gcagcctcaa   1920
cccgcgccag gccaggtttg cggaggaggc gtgcgcgctg ctgacgtcct cgaagttcga   1980
gccctgccac cgagcggtgg gtcctcagcc ctacgtgcag aactgcctct acgacgtctg   2040
ctcctgctcc gacggcagag actgtctttg cagcgccgtg gccaactacg ccgcagccgt   2100
ggcccggagg ggcgtgcaca tcgcgtggcg ggagccgggc ttctgtgcgc tgagctgccc   2160
ccagggccag gtgtacctgc agtgtgggac cccctgcaac atgacctgtc tctccctctc   2220
ttacccggag gaggactgca atgaggtctg cttggaaagc tgcttctccc cccagggct    2280 gtacctggat gagaggggag attgtgtgcc caaggctcag tgtccctgtt actatgatgg   2340
tgagatcttt cagcccgaag acatcttctc agaccatcac accatgtgct actgtgagga   2400
tggcttcatg cactgtacca caagtggagg cctgggaagc tgctgcccca acccggtgct   2460
cagcagcccc cggtgtcacc gcagcaaaag gagcctgtcc tgtcggcccc ccatggtcaa   2520
```

-continued

```
gttggtgtgt cccgctgata acccgagggc tgaaggactg agtgtgccaa aaacctgcca    2580
gaactatgac ctgcagtgca tgagcacagg ctgtgtctcc ggctgcctct gcccgcaggg    2640
catggtccgg catgaaaaca ggtgtgtggc gctggaaaga tgtccctgct tccaccaagg    2700
ccaagagtac gccccaggag aaaccgtgaa aattgactgc aacacttgtg tctgtcggga    2760
ccggaagtgg acctgcacag accatgtgtg tgatgccact tgctctgcca tcggcatggc    2820
gcactacctc accttcgacg gactcaagta cctgttccct ggggagtgcc agtatgttct    2880
ggtgcaggat tactgcggca gtaaccctgg gaccttacgg atcctggtgg ggaacgaggg    2940
gtgcagctac ccctcagtga atgcaagaa gcgggtcacc atcctggtgg aaggaggaga    3000
gattgaactt tttgatgggg aggtgaatgt gaagaaaccc atgaaggatg agactcactt    3060
tgaggtggta gagtctggtc agtacgtcat tctgctgctg ggcaaggcac tctctgtggt    3120
ctgggaccac cgcctgagca tctctgtgac cctgaagcgg acataccagg agcaggtgtg    3180
tggcctgtgt gggaattttg atggcatcca gaacaatgat ttcaccagca gcagcctcca    3240
aatagaagaa gaccctgtgg actttgggaa ttcctggaaa gtgaacccgc agtgtgccga    3300
caccaagaaa gtaccactgg actcatcccc tgccgtctgc cacaacaaca tcatgaagca    3360
gacgatggtg gattcctcct gcaggatcct caccagtgat attttccagg actgcaacag    3420
gctggtggac cctgagccat tcctggacat ttgcatctac acacttgct cctgtgagtc    3480
cattggggac tgcacctgct ctctgtgacac cattgctgct tacgcccacg tctgtgccca    3540
gcatggcaag gtggtagcct ggaggacagc cacattctgt ccccagaatt gcgaggagcg    3600
gaatctccac gagaatgggt atgagtgtga gtggcgctat aacagctgtg cccctgcctg    3660
tcccatcacg tgccagcacc ccgagccact ggcatgccct gtacagtgtg ttgaaggttg    3720
ccatgcgcac tgccctccag ggaaaatcct ggatgagctt ttgcagacct gcatcgaccc    3780
tgaagactgt cctgtgtgtg aggtggctgg tcgtcgcttg gccccaggaa agaaaatcat    3840
cttgaacccc agtgaccctg agcactgcca aatttgtaat tgtgatggtg tcaacttcac    3900
ctgtaaggcc tgcagagaac ccggaagtgt tgtggtgccc ccacagatg gccccattgg    3960
ctctaccacc tcgtatgtgg aggacacgtc ggagccgccc ctccatgact ccactgcag    4020
caggcttctg gacctggttt tcctgctgga tggctcctcc aagctgtctg aggacgagtt    4080
tgaagtgctg aaggtctttg tggtgggtat gatggagcat ctgcacatct cccagaagcg    4140
gatccgcgtg gctgtggtgg agtaccacga cggctcccac gcctacatcg agctcaagga    4200
ccggaagcga ccctcagagc tgcggcgcat caccagccag gtgaagtacg cgggcagcga    4260
ggtggcctcc accagtgagg tcttaaagta cacgctgttc cagatctttg gcaagatcga    4320
ccgcccggaa gcgtctcgca ttgccctgct cctgatggcc agccaggagc cctcaaggct    4380
ggcccggaat ttggtccgct atgtgcaggg cctgaagaag aagaaagtca ttgtcatccc    4440
tgtgggcatc gggccccacg ccagccttaa gcagatccac ctcatagaga agcaggcccc    4500
tgagaacaag gcctttgtgt tcagtggtgt ggatgagttg gagcagcgaa gggatgagat    4560
tatcaactac ctctgtgacc ttgccccga agcacctgcc cctactcagc acccccaat    4620
ggcccaggtc acggtgggtt cggagctgtt gggggttca tctccaggac caaaaggaa    4680
ctccatggtc ctggatgtgg tgtttgtcct ggaagggtca gacaaaattg gtgaggccaa    4740
cttttaacaaa agcagggagt tcatggagga ggtgattcag cggatggacg tgggccagga    4800
caggatccac gtcacagtgc tgcagtactc gtacatggtg accgtggagt acaccttcag    4860
```

|   |   |   |   |   |   |
|---|---|---|---|---|---|
| cgaggcgcag | tccaagggcg | aggtcctaca | gcaggtgcgg | gatatccgat | accggggtgg | 4920 |
| caacaggacc | aacactggac | tggccctgca | atacctgtcc | gaacacagct | tctcggtcag | 4980 |
| ccaggggggac | cgggagcagg | tacctaacct | ggtctacatg | gtcacaggaa | accccgcttc | 5040 |
| tgatgagatc | aagcggatgc | ctggagacat | ccaggtggtg | cccatcgggg | tgggtccaca | 5100 |
| tgccaatgtg | caggagctgg | agaagattgg | ctggcccaat | gccccatcc | tcatccatga | 5160 |
| ctttgagatg | ctccctcgag | aggctcctga | tctggtgcta | cagaggtgct | gctctggaga | 5220 |
| ggggctgcag | atccccaccc | tctcccccac | cccagattgc | agccagcccc | tggatgtggt | 5280 |
| cctcctcctg | gatggctctt | ccagcattcc | agcttcttac | tttgatgaaa | tgaagagctt | 5340 |
| caccaaggct | tttatttcaa | gagctaatat | agggccccgg | ctcactcaag | tgtcggtgct | 5400 |
| gcaatatgga | agcatcacca | ctatcgatgt | gccttggaat | gtagcctatg | agaaagtcca | 5460 |
| tttactgagc | cttgtggacc | tcatgcagca | ggagggaggc | cccagcgaaa | ttggggatgc | 5520 |
| tttgagcttt | gccgtgcgat | atgtcacctc | agaagtccat | ggtgccaggc | ccggagcctc | 5580 |
| gaaagcggtg | gttatcctag | tcacagatgt | ctccgtggat | tcagtggatg | ctgcagccga | 5640 |
| ggccgccaga | tccaaccgag | tgacagtgtt | ccccattgga | atcggggatc | ggtacagtga | 5700 |
| ggcccagctg | agcagcttgg | caggcccaaa | ggctggctcc | aatatggtaa | ggctccagcg | 5760 |
| aattgaagac | ctccccaccg | tggccaccct | gggaaattcc | ttcttccaca | agctgtgctc | 5820 |
| tgggtttgat | agagtttgcg | tggatgagga | tgggaatgag | aagaggcccg | gggatgtctg | 5880 |
| gaccttgcca | gaccagtgcc | acacagtgac | ttgcctgcca | gatggccaga | ccttgctgaa | 5940 |
| gagtcatcgg | gtcaactgtg | accggggggcc | aaggccttcg | tgccccaatg | gccagccccc | 6000 |
| tctcagggta | gaggagacct | gtggctgccg | ctggacctgt | ccctgtgtgt | gcatgggcag | 6060 |
| ctctacccgg | cacatcgtga | cctttgatgg | gcagaatttc | aagctgactg | gcagctgttc | 6120 |
| gtatgtccta | tttcaaaaca | aggagcagga | cctggaggtg | attctccaga | atggtgcctg | 6180 |
| cagccctggg | gcgaaggaga | cctgcatgaa | atccattgag | gtgaagcatg | acggcctctc | 6240 |
| agttgagctc | cacagtgaca | tgcagatgac | agtgaatggg | agactagtct | ccatcccata | 6300 |
| tgtgggtgga | gacatggaag | tcaatgttta | tgggaccatc | atgtatgagg | tcagattcaa | 6360 |
| ccatcttggc | cacatcttca | cattcacccc | ccaaaacaat | gagttccagc | tgcagctcag | 6420 |
| ccccaggacc | tttgcttcga | agacatatgg | tctctgtggg | atctgtgatg | agaacggagc | 6480 |
| caatgacttc | attctgaggg | atgggacagt | caccacagac | tggaaggcac | tcatccagga | 6540 |
| atggaccgta | cagcagcttg | ggaagacatc | ccagcctgtc | catgaggagc | agtgtcctgt | 6600 |
| ctccgaattc | ttccactgcc | aggtcctcct | ctcagaattg | tttgccgagt | gccacaaggt | 6660 |
| cctcgctcca | gccacctttt | atgccatgtg | ccagcccgac | agttgccacc | cgaagaaagt | 6720 |
| gtgtgaggcg | attgccttgt | atgcccacct | ctgtcggacc | aaagggggtct | gtgtggactg | 6780 |
| gaggagggcc | aatttctgtg | ctatgtcatg | tccaccatcc | ctggtgtaca | accactgtga | 6840 |
| gcatggctgc | cctcggctct | gtgaaggcaa | tacaagctcc | tgtgggggacc | aaccctcgga | 6900 |
| aggctgcttc | tgccccccaa | accaagtcat | gctggaaggt | agctgtgtcc | ccgaggaggc | 6960 |
| ctgtacccag | tgcatcagcg | aggatggagt | ccggcaccag | ttcctggaaa | cctgggtccc | 7020 |
| agcccaccag | ccttgccaga | tctgcacgtg | cctcagtggg | cggaaggtca | actgtacgtt | 7080 |
| gcagccctgc | cccacagcca | aagctcccac | ctgtggcccg | tgtgaagtgg | cccgcctccg | 7140 |
| ccagaacgca | gtgcagtgct | gcccggagta | cgagtgtgtg | tgtgacctgg | tgagctgtga | 7200 |
| cctgcccccg | gtgcctccct | gcgaagatgg | cctccagatg | accctgacca | atcctggcga | 7260 |

-continued

```
gtgcagaccc aacttcacct gtgcctgcag gaaggatgaa tgcagacggg agtccccgcc    7320
ctcttgtccc ccgcaccgga cgccggccct tcggaagact cagtgctgtg atgagtatga    7380
gtgtgcatgc aactgtgtca actccacggt gagctgcccg cttgggtacc tggcctcggc    7440
tgtcaccaac gactgtggct gcaccacaac aacctgcttc cctgacaagg tgtgtgtcca    7500
ccgaggcacc atctaccctg tgggccagtt ctgggaggag gcctgtgacg tgtgcacctg    7560
cacggacttg gaggactctg tgatgggcct gcgtgtggcc cagtgctccc agaagccctg    7620
tgaggacaac tgcctgtcag gcttcactta tgtccttcat gaaggcgagt gctgtggaag    7680
gtgtctgcca tctgcctgtg aggtggtcac tggttcacca cggggcgacg cccagtctca    7740
ctggaagaat gttggctctc actgggcctc ccctgacaac ccctgcctca tcaatgagtg    7800
tgtccgagtg aaggaagagg tctttgtgca acagaggaat gtctcctgcc cccagctgaa    7860
tgtccccacc tgccccacgg gcttccagct gagctgtaag acctcagagt gttgtcccac    7920
ctgtcactgc gagcccctgg aggcctgctt gctcaatggt accatcattg ggccggggaa    7980
aagtctgatg attgatgtgt gtacaacctg ccgctgcacc gtgccggtgg gagtcatctc    8040
tggattcaag ctggagggca ggaagaccac ctgtgaggca tgccccctgg gttataagga    8100
agagaagaac caaggtgaat gctgtgggag atgtctgcct atagcttgca ccattcagct    8160
aagaggagga cagatcatga cactgaagcg tgatgagact atccaggatg gctgtgacag    8220
tcacttctgc aaggtcaatg aaagaggaga gtacatctgg gagaagagag tcacgggttg    8280
cccacctttc gatgaacaca gtgtctggc tgagggagga aaaatcatga aaattccagg    8340
cacctgctgt gacacatgtg aggagccaga atgcaaggat atcattgcca agctgcagcg    8400
tgtcaaagtg ggagactgta agtctgaaga ggaagtggac attcattact gtgagggtaa    8460
atgtgccagc aaagccgtgt actccatcca catggaggat gtgcaggacc agtgctcctg    8520
ctgctcgccc acccagacgg agcccatgca ggtggccctg cgctgcacca atggctccct    8580
catctaccat gagatcctca atgccatcga atgcaggtgt tcccccagga agtgcagcaa    8640
gtgaggccac tgcctggatg ctactgtcgc ctgccttacc cgacctcact ggactggcca    8700
gagtgctgct cagtcctcct cagtcctcct cctgctctgc tcttgtgctt cctgatccca    8760
caataaaggt caatctttca ccttgaaaaa aaaaaaaaaa aa    8802
```

<210> SEQ ID NO 2
<211> LENGTH: 2813
<212> TYPE: PRT
<213> ORGANISM: Canis familiaris
<400> SEQUENCE: 2

```
Met Ser Pro Thr Arg Leu Val Arg Val Leu Leu Ala Leu Ala Leu Ile
 1               5                  10                  15

Leu Pro Gly Lys Leu Cys Thr Lys Gly Thr Val Gly Arg Ser Ser Met
            20                  25                  30

Ala Arg Cys Ser Leu Leu Gly Gly Asp Phe Ile Asn Thr Phe Asp Glu
        35                  40                  45

Ser Met Tyr Ser Phe Ala Gly Asp Cys Ser Tyr Leu Leu Ala Gly Asp
    50                  55                  60

Cys Gln Glu His Ser Ile Ser Leu Ile Gly Gly Phe Gln Asn Asp Lys
65                  70                  75                  80

Arg Val Ser Leu Ser Val Tyr Leu Gly Glu Phe Phe Asp Ile His Leu
                85                  90                  95
```

-continued

```
Phe Val Asn Gly Thr Met Leu Gln Gly Thr Gln Ser Ile Ser Met Pro
            100                 105                 110

Tyr Ala Ser Asn Gly Leu Tyr Leu Glu Ala Glu Ala Gly Tyr Tyr Lys
            115                 120                 125

Leu Ser Ser Glu Ala Tyr Gly Phe Val Ala Arg Ile Asp Gly Asn Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Lys Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Arg Cys Lys Arg Val Ser Pro Pro Ser Ser
            195                 200                 205

Pro Cys Asn Val Ser Ser Asp Glu Val Gln Gln Val Leu Trp Glu Gln
    210                 215                 220

Cys Gln Leu Leu Lys Ser Ala Ser Val Phe Ala Arg Cys His Pro Leu
225                 230                 235                 240

Val Asp Pro Glu Pro Phe Val Ala Leu Cys Glu Arg Thr Leu Cys Thr
                245                 250                 255

Cys Val Gln Gly Met Glu Cys Pro Cys Ala Val Leu Leu Glu Tyr Ala
            260                 265                 270

Arg Ala Cys Ala Gln Gln Gly Ile Val Leu Tyr Gly Trp Thr Asp His
            275                 280                 285

Ser Val Cys Arg Pro Ala Cys Pro Ala Gly Met Glu Tyr Lys Glu Cys
    290                 295                 300

Val Ser Pro Cys Thr Arg Thr Cys Gln Ser Leu His Val Lys Glu Val
305                 310                 315                 320

Cys Gln Glu Gln Cys Val Asp Gly Cys Ser Cys Pro Glu Gly Gln Leu
                325                 330                 335

Leu Asp Glu Gly His Cys Val Gly Ser Ala Glu Cys Ser Cys Val His
            340                 345                 350

Ala Gly Gln Arg Tyr Pro Pro Gly Ala Ser Leu Leu Gln Asp Cys His
            355                 360                 365

Thr Cys Ile Cys Arg Asn Ser Leu Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Val Cys His Tyr Leu Leu Ala Gln
                405                 410                 415

Asp Cys Gln Asp His Thr Phe Ser Val Val Ile Glu Thr Val Gln Cys
            420                 425                 430

Ala Asp Asp Leu Asp Ala Val Cys Thr Arg Ser Val Thr Val Arg Leu
            435                 440                 445

Pro Gly His His Asn Ser Leu Val Lys Leu Lys Asn Gly Gly Gly Val
    450                 455                 460

Ser Met Asp Gly Gln Asp Ile Gln Ile Pro Leu Leu Gln Gly Asp Leu
465                 470                 475                 480

Arg Ile Gln His Thr Val Met Ala Ser Val Arg Leu Ser Tyr Gly Glu
                485                 490                 495

Asp Leu Gln Met Asp Ser Asp Val Arg Gly Arg Leu Leu Val Thr Leu
            500                 505                 510

Tyr Pro Ala Tyr Ala Gly Lys Thr Cys Gly Arg Gly Gly Asn Tyr Asn
```

-continued

```
                515                 520                 525
Gly Asn Arg Gly Asp Asp Phe Val Thr Pro Ala Gly Leu Ala Glu Pro
            530                 535                 540
Leu Val Glu Asp Phe Gly Asn Ala Trp Lys Leu Leu Gly Ala Cys Glu
545                 550                 555                 560
Asn Leu Gln Lys Gln His Arg Asp Pro Cys Ser Leu Asn Pro Arg Gln
                565                 570                 575
Ala Arg Phe Ala Glu Glu Ala Cys Ala Leu Leu Thr Ser Ser Lys Phe
            580                 585                 590
Glu Pro Cys His Arg Ala Val Gly Pro Gln Pro Tyr Val Gln Asn Cys
        595                 600                 605
Leu Tyr Asp Val Cys Ser Cys Ser Asp Gly Arg Asp Cys Leu Cys Ser
        610                 615                 620
Ala Val Ala Asn Tyr Ala Ala Ala Val Ala Arg Arg Gly Val His Ile
625                 630                 635                 640
Ala Trp Arg Glu Pro Gly Phe Cys Ala Leu Ser Cys Pro Gln Gly Gln
            645                 650                 655
Val Tyr Leu Gln Cys Gly Thr Pro Cys Asn Met Thr Cys Leu Ser Leu
            660                 665                 670
Ser Tyr Pro Glu Glu Asp Cys Asn Glu Val Cys Leu Glu Ser Cys Phe
        675                 680                 685
Ser Pro Pro Gly Leu Tyr Leu Asp Glu Arg Gly Asp Cys Val Pro Lys
        690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Thr Ser Gly Gly Leu Gly Ser Leu Leu Pro Asn Pro Val
            740                 745                 750
Leu Ser Ser Pro Arg Cys His Arg Ser Lys Arg Ser Leu Ser Cys Arg
        755                 760                 765
Pro Pro Met Val Lys Leu Val Cys Pro Ala Asp Asn Pro Arg Ala Glu
    770                 775                 780
Gly Leu Glu Cys Ala Lys Thr Cys Gln Asn Tyr Asp Leu Gln Cys Met
785                 790                 795                 800
Ser Thr Gly Cys Val Ser Gly Cys Leu Cys Pro Gln Gly Met Val Arg
                805                 810                 815
His Glu Asn Arg Cys Val Ala Leu Glu Arg Cys Pro Cys Phe His Gln
            820                 825                 830
Gly Gln Glu Tyr Ala Pro Gly Glu Thr Val Lys Ile Asp Cys Asn Thr
        835                 840                 845
Cys Val Cys Arg Asp Arg Lys Trp Thr Cys Thr Asp His Val Cys Asp
    850                 855                 860
Ala Thr Cys Ser Ala Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
            885                 890                 895
Tyr Cys Gly Ser Asn Pro Gly Thr Leu Arg Ile Leu Val Gly Asn Glu
            900                 905                 910
Gly Cys Ser Tyr Pro Ser Val Lys Cys Lys Lys Arg Val Thr Ile Leu
        915                 920                 925
Val Glu Gly Gly Glu Ile Glu Leu Phe Asp Gly Glu Val Asn Val Lys
930                 935                 940
```

-continued

```
Lys Pro Met Lys Asp Glu Thr His Phe Glu Val Val Glu Ser Gly Gln
945                 950                 955                 960

Tyr Val Ile Leu Leu Leu Gly Lys Ala Leu Ser Val Val Trp Asp His
            965                 970                 975

Arg Leu Ser Ile Ser Val Thr Leu Lys Arg Thr Tyr Gln Glu Gln Val
        980                 985                 990

Cys Gly Leu Cys Gly Asn Phe Asp Gly Ile Gln Asn Asn Asp Phe Thr
    995                 1000                1005

Ser Ser Ser Leu Gln Ile Glu Glu Asp Pro Val Asp Phe Gly Asn Ser
1010                1015                1020

Trp Lys Val Asn Pro Gln Cys Ala Asp Thr Lys Lys Val Pro Leu Asp
1025                1030                1035                1040

Ser Ser Pro Ala Val Cys His Asn Asn Ile Met Lys Gln Thr Met Val
                1045                1050                1055

Asp Ser Ser Cys Arg Ile Leu Thr Ser Asp Ile Phe Gln Asp Cys Asn
            1060                1065                1070

Arg Leu Val Asp Pro Glu Pro Phe Leu Asp Ile Cys Ile Tyr Asp Thr
        1075                1080                1085

Cys Ser Cys Glu Ser Ile Gly Asp Cys Thr Cys Phe Cys Asp Thr Ile
    1090                1095                1100

Ala Ala Tyr Ala His Val Cys Ala Gln His Gly Lys Val Val Ala Trp
1105                1110                1115                1120

Arg Thr Ala Thr Phe Cys Pro Gln Asn Cys Glu Glu Arg Asn Leu His
                1125                1130                1135

Glu Asn Gly Tyr Glu Cys Glu Trp Arg Tyr Asn Ser Cys Ala Pro Ala
            1140                1145                1150

Cys Pro Ile Thr Cys Gln His Pro Glu Pro Leu Ala Cys Pro Val Gln
        1155                1160                1165

Cys Val Glu Gly Cys His Ala His Cys Pro Pro Gly Lys Ile Leu Asp
    1170                1175                1180

Glu Leu Leu Gln Thr Cys Ile Asp Pro Glu Asp Cys Pro Val Cys Glu
1185                1190                1195                1200

Val Ala Gly Arg Arg Leu Ala Pro Gly Lys Lys Ile Ile Leu Asn Pro
                1205                1210                1215

Ser Asp Pro Glu His Cys Gln Ile Cys Asn Cys Asp Gly Val Asn Phe
            1220                1225                1230

Thr Cys Lys Ala Cys Arg Glu Pro Gly Ser Val Val Pro Pro Thr
        1235                1240                1245

Asp Gly Pro Ile Gly Ser Thr Thr Ser Tyr Val Glu Asp Thr Ser Glu
1250                1255                1260

Pro Pro Leu His Asp Phe His Cys Ser Arg Leu Leu Asp Leu Val Phe
1265                1270                1275                1280

Leu Leu Asp Gly Ser Ser Lys Leu Ser Glu Asp Glu Phe Glu Val Leu
            1285                1290                1295

Lys Val Phe Val Val Gly Met Met Glu His Leu His Ile Ser Gln Lys
        1300                1305                1310

Arg Ile Arg Val Ala Val Val Glu Tyr His Asp Gly Ser His Ala Tyr
    1315                1320                1325

Ile Glu Leu Lys Asp Arg Lys Arg Pro Ser Glu Leu Arg Arg Ile Thr
1330                1335                1340

Ser Gln Val Lys Tyr Ala Gly Ser Glu Val Ala Ser Thr Ser Glu Val
1345                1350                1355                1360
```

-continued

Leu Lys Tyr Thr Leu Phe Gln Ile Phe Gly Lys Ile Asp Arg Pro Glu
        1365                1370                1375

Ala Ser Arg Ile Ala Leu Leu Met Ala Ser Gln Glu Pro Ser Arg
    1380                1385                1390

Leu Ala Arg Asn Leu Val Arg Tyr Val Gln Gly Leu Lys Lys Lys
1395                1400                1405

Val Ile Val Ile Pro Val Gly Ile Gly Pro His Ala Ser Leu Lys Gln
    1410                1415                1420

Ile His Leu Ile Glu Lys Gln Ala Pro Glu Asn Lys Ala Phe Val Phe
1425                1430                1435                1440

Ser Gly Val Asp Glu Leu Glu Gln Arg Arg Asp Glu Ile Ile Asn Tyr
            1445                1450                1455

Leu Cys Asp Leu Ala Pro Glu Ala Pro Ala Pro Thr Gln His Pro Pro
            1460                1465                1470

Met Ala Gln Val Thr Val Gly Ser Glu Leu Leu Gly Val Ser Ser Pro
    1475                1480                1485

Gly Pro Lys Arg Asn Ser Met Val Leu Asp Val Val Phe Val Leu Glu
    1490                1495                1500

Gly Ser Asp Lys Ile Gly Glu Ala Asn Phe Asn Lys Ser Arg Glu Phe
1505                1510                1515                1520

Met Glu Glu Val Ile Gln Arg Met Asp Val Gly Gln Asp Arg Ile His
            1525                1530                1535

Val Thr Val Leu Gln Tyr Ser Tyr Met Val Thr Val Glu Tyr Thr Phe
            1540                1545                1550

Ser Glu Ala Gln Ser Lys Gly Glu Val Leu Gln Gln Val Arg Asp Ile
        1555                1560                1565

Arg Tyr Arg Gly Gly Asn Arg Thr Asn Thr Gly Leu Ala Leu Gln Tyr
    1570                1575                1580

Leu Ser Glu His Ser Phe Ser Val Ser Gln Gly Asp Arg Glu Gln Val
1585                1590                1595                1600

Pro Asn Leu Val Tyr Met Val Thr Gly Asn Pro Ala Ser Asp Glu Ile
            1605                1610                1615

Lys Arg Met Pro Gly Asp Ile Gln Val Val Pro Ile Gly Val Gly Pro
            1620                1625                1630

His Ala Asn Val Gln Glu Leu Glu Lys Ile Gly Trp Pro Asn Ala Pro
        1635                1640                1645

Ile Leu Ile His Asp Phe Glu Met Leu Pro Arg Glu Ala Pro Asp Leu
    1650                1655                1660

Val Leu Gln Arg Cys Cys Ser Gly Glu Gly Leu Gln Ile Pro Thr Leu
1665                1670                1675                1680

Ser Pro Thr Pro Asp Cys Ser Gln Pro Leu Asp Val Val Leu Leu Leu
            1685                1690                1695

Asp Gly Ser Ser Ser Ile Pro Ala Ser Tyr Phe Asp Glu Met Lys Ser
            1700                1705                1710

Phe Thr Lys Ala Phe Ile Ser Arg Ala Asn Ile Gly Pro Arg Leu Thr
        1715                1720                1725

Gln Val Ser Val Leu Gln Tyr Gly Ser Ile Thr Thr Ile Asp Val Pro
    1730                1735                1740

Trp Asn Val Ala Tyr Glu Lys Val His Leu Leu Ser Leu Val Asp Leu
1745                1750                1755                1760

Met Gln Gln Glu Gly Gly Pro Ser Glu Ile Gly Asp Ala Leu Ser Phe
            1765                1770                1775

Ala Val Arg Tyr Val Thr Ser Glu Val His Gly Ala Arg Pro Gly Ala

-continued

```
                     1780                1785                1790
Ser Lys Ala Val Val Ile Leu Val Thr Asp Val Ser Val Asp Ser Val
         1795                1800                1805

Asp Ala Ala Ala Glu Ala Ala Arg Ser Asn Arg Val Thr Val Phe Pro
     1810                1815                1820

Ile Gly Ile Gly Asp Arg Tyr Ser Glu Ala Gln Leu Ser Ser Leu Ala
1825                1830                1835                1840

Gly Pro Lys Ala Gly Ser Asn Met Val Arg Leu Gln Arg Ile Glu Asp
             1845                1850                1855

Leu Pro Thr Val Ala Thr Leu Gly Asn Ser Phe Phe His Lys Leu Cys
         1860                1865                1870

Ser Gly Phe Asp Arg Val Cys Val Asp Glu Asp Gly Asn Glu Lys Arg
         1875                1880                1885

Pro Gly Asp Val Trp Thr Leu Pro Asp Gln Cys His Thr Val Thr Cys
         1890                1895                1900

Leu Pro Asp Gly Gln Thr Leu Leu Lys Ser His Arg Val Asn Cys Asp
1905                1910                1915                1920

Arg Gly Pro Arg Pro Ser Cys Pro Asn Gly Gln Pro Pro Leu Arg Val
             1925                1930                1935

Glu Glu Thr Cys Gly Cys Arg Trp Thr Cys Pro Cys Val Cys Met Gly
         1940                1945                1950

Ser Ser Thr Arg His Ile Val Thr Phe Asp Gly Gln Asn Phe Lys Leu
         1955                1960                1965

Thr Gly Ser Cys Ser Tyr Val Leu Phe Gln Asn Lys Glu Gln Asp Leu
     1970                1975                1980

Glu Val Ile Leu Gln Asn Gly Ala Cys Ser Pro Gly Ala Lys Glu Thr
1985                1990                1995                2000

Cys Met Lys Ser Ile Glu Val Lys His Asp Gly Leu Ser Val Glu Leu
             2005                2010                2015

His Ser Asp Met Gln Met Thr Val Asn Gly Arg Leu Val Ser Ile Pro
             2020                2025                2030

Tyr Val Gly Gly Asp Met Glu Val Asn Val Tyr Gly Thr Ile Met Tyr
         2035                2040                2045

Glu Val Arg Phe Asn His Leu Gly His Ile Phe Thr Phe Thr Pro Gln
     2050                2055                2060

Asn Asn Glu Phe Gln Leu Gln Leu Ser Pro Arg Thr Phe Ala Ser Lys
2065                2070                2075                2080

Thr Tyr Gly Leu Cys Gly Ile Cys Asp Glu Asn Gly Ala Asn Asp Phe
             2085                2090                2095

Ile Leu Arg Asp Gly Thr Val Thr Thr Asp Trp Lys Ala Leu Ile Gln
             2100                2105                2110

Glu Trp Thr Val Gln Gln Leu Gly Lys Thr Ser Gln Pro Val His Glu
         2115                2120                2125

Glu Gln Cys Pro Val Ser Glu Phe Phe His Cys Gln Val Leu Leu Ser
     2130                2135                2140

Glu Leu Phe Ala Glu Cys His Lys Val Leu Ala Pro Ala Thr Phe Tyr
2145                2150                2155                2160

Ala Met Cys Gln Pro Asp Ser Cys His Pro Lys Lys Val Cys Glu Ala
             2165                2170                2175

Ile Ala Leu Tyr Ala His Leu Cys Arg Thr Lys Gly Val Cys Val Asp
             2180                2185                2190

Trp Arg Arg Ala Asn Phe Cys Ala Met Ser Cys Pro Pro Ser Leu Val
         2195                2200                2205
```

```
Tyr Asn His Cys Glu His Gly Cys Pro Arg Leu Cys Glu Gly Asn Thr
    2210                2215                2220
Ser Ser Cys Gly Asp Gln Pro Ser Glu Gly Cys Phe Cys Pro Pro Asn
2225                2230                2235                2240
Gln Val Met Leu Glu Gly Ser Cys Val Pro Glu Ala Cys Thr Gln
            2245                2250                2255
Cys Ile Ser Glu Asp Gly Val Arg His Gln Phe Leu Glu Thr Trp Val
            2260                2265                2270
Pro Ala His Gln Pro Cys Gln Ile Cys Thr Cys Leu Ser Gly Arg Lys
        2275                2280                2285
Val Asn Cys Thr Leu Gln Pro Cys Pro Thr Ala Lys Ala Pro Thr Cys
    2290                2295                2300
Gly Pro Cys Glu Val Ala Arg Leu Arg Gln Asn Ala Val Gln Cys Cys
2305                2310                2315                2320
Pro Glu Tyr Glu Cys Val Cys Asp Leu Val Ser Cys Asp Leu Pro Pro
            2325                2330                2335
Val Pro Pro Cys Glu Asp Gly Leu Gln Met Thr Leu Thr Asn Pro Gly
            2340                2345                2350
Glu Cys Arg Pro Asn Phe Thr Cys Ala Cys Arg Lys Asp Glu Cys Arg
        2355                2360                2365
Arg Glu Ser Pro Pro Ser Cys Pro Pro His Arg Thr Pro Ala Leu Arg
    2370                2375                2380
Lys Thr Gln Cys Cys Asp Glu Tyr Glu Cys Ala Cys Asn Cys Val Asn
2385                2390                2395                2400
Ser Thr Val Ser Cys Pro Leu Gly Tyr Leu Ala Ser Ala Val Thr Asn
            2405                2410                2415
Asp Cys Gly Cys Thr Thr Thr Thr Cys Phe Pro Asp Lys Val Cys Val
            2420                2425                2430
His Arg Gly Thr Ile Tyr Pro Val Gly Gln Phe Trp Glu Glu Ala Cys
        2435                2440                2445
Asp Val Cys Thr Cys Thr Asp Leu Glu Asp Ser Val Met Gly Leu Arg
    2450                2455                2460
Val Ala Gln Cys Ser Gln Lys Pro Cys Glu Asp Asn Cys Leu Ser Gly
2465                2470                2475                2480
Phe Thr Tyr Val Leu His Glu Gly Glu Cys Cys Gly Arg Cys Leu Pro
            2485                2490                2495
Ser Ala Cys Glu Val Val Thr Gly Ser Pro Arg Gly Asp Ala Gln Ser
            2500                2505                2510
His Trp Lys Asn Val Gly Ser His Trp Ala Ser Pro Asp Asn Pro Cys
        2515                2520                2525
Leu Ile Asn Glu Cys Val Arg Val Lys Glu Glu Val Phe Val Gln Gln
    2530                2535                2540
Arg Asn Val Ser Cys Pro Gln Leu Asn Val Pro Thr Cys Pro Thr Gly
2545                2550                2555                2560
Phe Gln Leu Ser Cys Lys Thr Ser Glu Cys Cys Pro Thr Cys His Cys
            2565                2570                2575
Glu Pro Leu Glu Ala Cys Leu Leu Asn Gly Thr Ile Ile Gly Pro Gly
            2580                2585                2590
Lys Ser Leu Met Ile Asp Val Cys Thr Thr Cys Arg Cys Thr Val Pro
        2595                2600                2605
Val Gly Val Ile Ser Gly Phe Lys Leu Glu Gly Arg Lys Thr Thr Cys
    2610                2615                2620
```

```
Glu Ala Cys Pro Leu Gly Tyr Lys Glu Glu Lys Asn Gln Gly Glu Cys
2625                2630                2635                2640

Cys Gly Arg Cys Leu Pro Ile Ala Cys Thr Ile Gln Leu Arg Gly Gly
            2645                2650                2655

Gln Ile Met Thr Leu Lys Arg Asp Glu Thr Ile Gln Asp Gly Cys Asp
        2660                2665                2670

Ser His Phe Cys Lys Val Asn Glu Arg Gly Glu Tyr Ile Trp Glu Lys
    2675                2680                2685

Arg Val Thr Gly Cys Pro Pro Phe Asp Glu His Lys Cys Leu Ala Glu
2690                2695                2700

Gly Gly Lys Ile Met Lys Ile Pro Gly Thr Cys Cys Asp Thr Cys Glu
2705                2710                2715                2720

Glu Pro Glu Cys Lys Asp Ile Ile Ala Lys Leu Gln Arg Val Lys Val
            2725                2730                2735

Gly Asp Cys Lys Ser Glu Glu Val Asp Ile His Tyr Cys Glu Gly
        2740                2745                2750

Lys Cys Ala Ser Lys Ala Val Tyr Ser Ile His Met Glu Asp Val Gln
    2755                2760                2765

Asp Gln Cys Ser Cys Cys Ser Pro Thr Gln Thr Glu Pro Met Gln Val
    2770                2775                2780

Ala Leu Arg Cys Thr Asn Gly Ser Leu Ile Tyr His Glu Ile Leu Asn
2785                2790                2795                2800

Ala Ile Glu Cys Arg Cys Ser Pro Arg Lys Cys Ser Lys
            2805                2810

<210> SEQ ID NO 3
<211> LENGTH: 60
<212> TYPE: DNA
<213> ORGANISM: Canis familiaris

<400> SEQUENCE: 3
aggggttttc caaaatgaca aaagagtgag cctctccgtg tatctcggag aattttttcga      60

<210> SEQ ID NO 4
<211> LENGTH: 60
<212> TYPE: DNA
<213> ORGANISM: Canis familiaris

<400> SEQUENCE: 4
cattcatttg tttgtcaatg gtaccatgct gcaggggacc caaaggtaag tcagaagccc      60

<210> SEQ ID NO 5
<211> LENGTH: 60
<212> TYPE: DNA
<213> ORGANISM: Canis familiaris

<400> SEQUENCE: 5
gaatgttcag gttaatatgg accctgggga tcactttgca accccttgt tttttcagat       60

<210> SEQ ID NO 6
<211> LENGTH: 60
<212> TYPE: DNA
<213> ORGANISM: Canis familiaris

<400> SEQUENCE: 6
gagggagccg gggcccagag acaggaagta aatgtgccca gggaaagtga gtggcaggac      60

<210> SEQ ID NO 7
<211> LENGTH: 60
```

```
<212> TYPE: DNA
<213> ORGANISM: Canis familiaris

<400> SEQUENCE: 7
tgggtgaaag cccatatcc cgactcctgg tcaaggagac tttgcaccaa ggtcccagcc    60

<210> SEQ ID NO 8
<211> LENGTH: 60
<212> TYPE: DNA
<213> ORGANISM: Canis familiaris

<400> SEQUENCE: 8
ctggagcatg gggttggggt tggaaggtgg agggacatgg aggaaatgca tgagaagcac    60

<210> SEQ ID NO 9
<211> LENGTH: 58
<212> TYPE: DNA
<213> ORGANISM: Canis familiaris

<400> SEQUENCE: 9
gcttcctgag ctcctccttg tcccaccagc atctccatgc cctacgcctc caatgggc     58

<210> SEQ ID NO 10
<211> LENGTH: 24
<212> TYPE: DNA
<213> ORGANISM: Canis familiaris

<400> SEQUENCE: 10
aaatgacaaa agagtgagcc ggtc                                          24

<210> SEQ ID NO 11
<211> LENGTH: 24
<212> TYPE: DNA
<213> ORGANISM: Canis familiaris

<400> SEQUENCE: 11
aagtctcctt gaccagcggt cggg                                          24

<210> SEQ ID NO 12
<211> LENGTH: 35
<212> TYPE: PRT
<213> ORGANISM: Canis familiaris

<400> SEQUENCE: 12

Gly Gly Phe Gln Asn Asp Lys Arg Val Ser Leu Ser Val Tyr Leu Gly
  1               5                  10                  15

Glu Phe Phe Asp Ile His Leu Phe Val Asn Gly Thr Met Leu Gln Gly
             20                  25                  30

Thr Gln Arg
         35

<210> SEQ ID NO 13
<211> LENGTH: 9
<212> TYPE: PRT
<213> ORGANISM: Canis familiaris

<400> SEQUENCE: 13

Ile Ser Met Pro Tyr Ala Ser Asn Gly
  1               5

<210> SEQ ID NO 14
<211> LENGTH: 31
<212> TYPE: DNA
```

<213> ORGANISM: Canis familiaris

<400> SEQUENCE: 14
aggacaactg cctgcctgtc ggtgagtggg g             31

<210> SEQ ID NO 15
<211> LENGTH: 31
<212> TYPE: DNA
<213> ORGANISM: Canis familiaris

<400> SEQUENCE: 15
aggacaactg cctgcctgtc agtgagtggg g             31

<210> SEQ ID NO 16
<211> LENGTH: 8
<212> TYPE: DNA
<213> ORGANISM: Canis familiaris

<400> SEQUENCE: 16 aggtragt                                        8

<210> SEQ ID NO 17
<211> LENGTH: 12
<212> TYPE: DNA
<213> ORGANISM: Canis familiaris

<400> SEQUENCE: 17
ggcttcactt at                                  12

<210> SEQ ID NO 18
<211> LENGTH: 18
<212> TYPE: DNA
<213> ORGANISM: Canis familiaris

<400> SEQUENCE: 18
aggacaactg cctggctt                            18

<210> SEQ ID NO 19
<211> LENGTH: 15
<212> TYPE: DNA
<213> ORGANISM: Canis familiaris

<400> SEQUENCE: 19
gagcctttgt cgccc                               15

<210> SEQ ID NO 20
<211> LENGTH: 16
<212> TYPE: DNA
<213> ORGANISM: Canis familiaris

<400> SEQUENCE: 20 gagcctttttg tcgccc                             16

<210> SEQ ID NO 21
<211> LENGTH: 218
<212> TYPE: DNA
<213> ORGANISM: Canis familiaris

<400> SEQUENCE: 21
gtcctgtggg agcagtgcca gctcctgaag agtgcctcgg tgtttgcccg ctgccacccg      60
ctggtggacc ctgagccttt tgtcgccctg tgtgaaagga ctctgtgcac ctgtgtccag     120
gggatggagt gcccttgtgc ggtcctcctg gagtacgccc gggcctgtgc ccagcaggga     180

```
attgtgctgt acggctggac cgaccacagc gtctgccg                         218
```

<210> SEQ ID NO 22
<211> LENGTH: 73
<212> TYPE: PRT
<213> ORGANISM: Canis familiaris

<400> SEQUENCE: 22

```
Val Leu Trp Glu Gln Cys Gln Leu Leu Lys Ser Ala Ser Val Phe Ala
 1               5                  10                  15

Arg Cys His Pro Leu Val Asp Pro Glu Pro Phe Val Ala Leu Cys Glu
            20                  25                  30

Arg Thr Leu Cys Thr Cys Val Gln Gly Met Glu Cys Pro Cys Ala Val
        35                  40                  45

Leu Leu Glu Tyr Ala Arg Ala Cys Ala Gln Gln Gly Ile Val Leu Tyr
    50                  55                  60

Gly Trp Thr Asp His Ser Val Cys Arg
 65                  70
```

<210> SEQ ID NO 23
<211> LENGTH: 20
<212> TYPE: DNA
<213> ORGANISM: Canis familiaris

<400> SEQUENCE: 23

```
tcctgtggga gcagtgccag                                             20
```

<210> SEQ ID NO 24
<211> LENGTH: 11
<212> TYPE: DNA
<213> ORGANISM: Canis familiaris
<220> FEATURE:
<221> NAME/KEY: misc_feature
<222> LOCATION: 3-9
<223> OTHER INFORMATION: n=a,c,t, or g

<400> SEQUENCE: 24

```
gcnnnnnnng c                                                      11
```

<210> SEQ ID NO 25
<211> LENGTH: 18
<212> TYPE: DNA
<213> ORGANISM: Canis familiaris

<400> SEQUENCE: 25

```
gtggtcggtc cagccgta                                               18
```

<210> SEQ ID NO 26
<211> LENGTH: 20
<212> TYPE: DNA
<213> ORGANISM: Canis familiaris

<400> SEQUENCE: 26

```
tctaccctgt gggccagttc                                             20
```

<210> SEQ ID NO 27
<211> LENGTH: 19
<212> TYPE: DNA
<213> ORGANISM: Canis familiaris

<400> SEQUENCE: 27

```
gaccacctca caggcagat                                              19
```

```
<210> SEQ ID NO 28
<211> LENGTH: 21
<212> TYPE: DNA
<213> ORGANISM: Canis familiaris

<400> SEQUENCE: 28
ctgtgaggac aactgcctgc c                                              21

<210> SEQ ID NO 29
<211> LENGTH: 26
<212> TYPE: DNA
<213> ORGANISM: Canis familiaris

<400> SEQUENCE: 29
tggccctgaa ccggaaatta ctcaag                                         26
```

DNA ENCODING CANINE VON WILLEBRAND FACTOR AND METHODS OF USE

RELATED APPLICATIONS

The present invention is a continuation of Ser. No. 09/662,478 filed Sep. 15, 2000 which is a continuation-in-part of U.S. Ser. No. 08/896,449, filed Jul. 18, 1997, now U.S. Pat. No. 6,040,143 which claims priority from U.S. Ser. No. 60/020,998, filed Jul. 19, 1996, both hereby expressly incorporated by reference.

FIELD OF THE INVENTION

This invention relates generally to canine von Willebrand factor (vWF), and more particularly, to the gene encoding vWF as well as a genetic defect that causes canine von Willebrand's disease.

BACKGROUND OF THE INVENTION

In both dogs and humans, von Willebrand's disease (vWD) is a bleeding disorder of variable severity that results from a quantitative or qualitative defect in von Willebrand factor (vWF) (Ginsburg, D. et al., *Blood* 79:2507–2519 (1992); Ruggeri, Z. M., et al., *FASEB J* 7:308–316 (1993); Dodds, W. J., *Mod Vet Pract* 681–686 (1984); Johnson, G. S. et al., *JAVMA* 176:1261–1263 (1988); Brooks, M., *Probl In Vet Med* 4:636–646 (1992)). This clotting factor has two known functions, stabilization of Factor VIII (hemophilic factor A) in the blood, and aiding the adhesion of platelets to the subendothelium, which allows them to provide hemostasis more effectively. If the factor is missing or defective, the patient, whether human or dog, may bleed severely.

The disease is the most common hereditary bleeding disorder in both species, and is genetically and clinically heterogenous. Three clinical types, called 1, 2, and 3 (formerly I, II, and III; see Sadler, J. E. et al., *Blood* 84:676–679 (1994) for nomenclature changes), have been described. Type 1 vWD is inherited in a dominant, incompletely penetrant fashion. Bleeding appears to be due to the reduced level of vWF rather than a qualitative difference. Although this is the most common form of vWD found in most mammals, and can cause serious bleeding problems, it is generally less severe than the other two types. In addition, a relatively inexpensive vasopressin analog (DDAVP) can help alleviate symptoms (Kraus, K. H. et al., *Vet Surg* 18:103–109 (1989)).

In Type 2 vWD, patients may have essentially normal levels of vWF, but the factor is abnormal as determined by specialized tests (Ruggeri, Z. M., et al., *FASEB J* 7:308–316 (1993); Brooks, M., *Probl In Vet Med* 4:636–646 (1992)). This type is also inherited in a dominant fashion and has only rarely been described in dogs (Turrentine, M. A., et al., *Vet Clin North Am Small Anim Pract* 18:275 (1988)).

Type 3 vWD is the most severe form of the disease. It is inherited as an autosomal recessive trait, and affected individuals have no detectable vWF in their blood. Serious bleeding episodes require transfusions of blood or cryoprecipitate to supply the missing vWF. Heterozygous carriers have moderately reduced factor concentrations, but generally appear to have normal hemostasis.

Scottish terriers have Type 3 vWD (Dodds, W. J., *Mod Vet Pract* 681–686 (1984); Johnson, G. S. et al., *JAVMA* 176:1261–1263 (1988)). Homozygotes have no detectable vWF and have a severe bleeding disorder. Heterozygotes have reduced levels of the factor, and are clinically normal (Brooks, M. et al., *JAVMA* 200:1123–1127 (1992)). The prevalence of vWD among Scottish terriers including both heterozygotes and homozygotes has been variously estimated from 27–31% (Stokol, T. et al., *Res. Vet. Sci.* 59:152–155 (1995); Brooks, M., *Proc. 9th ACVIM Forum* 89–91 (1991)).

Currently, detection of affected and carrier Scottish terrier dogs is done by vWF antigen testing (Benson, R. E, et al., *Am J Vet Res* 44:399–403 (1983); Stokol, T. et al., *Res. Vet. Sci.* 59:152–155 (1995)) or by coagulation assays (Rosborough, T. K. et al., *J. Lab. Clin. Med.* 96:47–56 (1980); Read, M. S. et al., *J. Lab. Clin. Med.* 101:74–82 (1983)). These procedures yield variable results, as the protein-based tests can be influenced by such things as sample collection, sample handling, estrous, pregnancy, vaccination, age, and hypothyroidism (Strauss, H. S. et al., *New Eng J Med* 269:1251–1252 (1963); Bloom, A. L., *Mayo Clin Proc* 66:743–751 (1991); Stirling, Y. et al., *Thromb Haemostasis* 52:176–182 (1984); Mansell, P. D. et al., *Br. Vet J.* 148:329–337 (1992); Avgeris, S. et al., *JAVMA* 196:921–924 (1990); Panciera, D. P. et al., *JAVMA* 205:1550–1553 (1994)). Thus, for example, a dog that tests within the normal range on one day, can test within the carrier range on another day. It is therefore difficult for breeders to use this information.

It would thus be desirable to provide the nucleic acid sequence encoding canine vWF. It would also be desirable to provide the genetic defect responsible for canine vWD. It would further be desirable to obtain the amino acid sequence of canine vWF. It would also be desirable to provide a method for detecting carriers of the defective vWF gene based on the nucleic acid sequence of the normal and defective vWF gene.

SUMMARY OF THE INVENTION

The present invention provides a novel purified and isolated nucleic acid sequence encoding canine vWF. Nucleic acid sequences containing the mutations that cause vWD in Scottish terriers, Doberman pinschers, Shetland sheepdogs, Manchester terriers and Poodles are also provided. The nucleic acid sequences of the present invention may be used in methods for detecting carriers of the mutation that causes vWD. Such methods may be used by breeders to reduce the frequency of the disease-causing allele and the incidence of disease. In addition, the nucleic acid sequence of the canine vWF provided herein may be used to determine the genetic defect that causes vWD in other breeds as well as other species.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIGS. 1A–1D is the nucleic acid sequence of the canine von Willebrand factor of the present invention (SEQ ID NO: 1);

FIGS. 2A–2D is a comparison of the human and canine prepro-von Willebrand factor amino acid sequences (SEQ ID NO: 2);

FIG. 4 illustrates the results of a method of the present invention used to detect the Scottish terrier vWD mutation (SEQ ID NOS: 3–13);

FIG. 6 is an illustration showing the splice site comparison between normal and mutant Doberman pinscher vWF alleles (SEQ ID NOS: 14–17);

FIG. 11 is a diagram illustrating the Mwo I diagnostic test for the Shetland sheepdog Type 3 vWD mutation (SEQ ID NOS: 21–25)

DETAILED DESCRIPTION OF THE PREFERRED EMBODIMENTS

Figure 3:
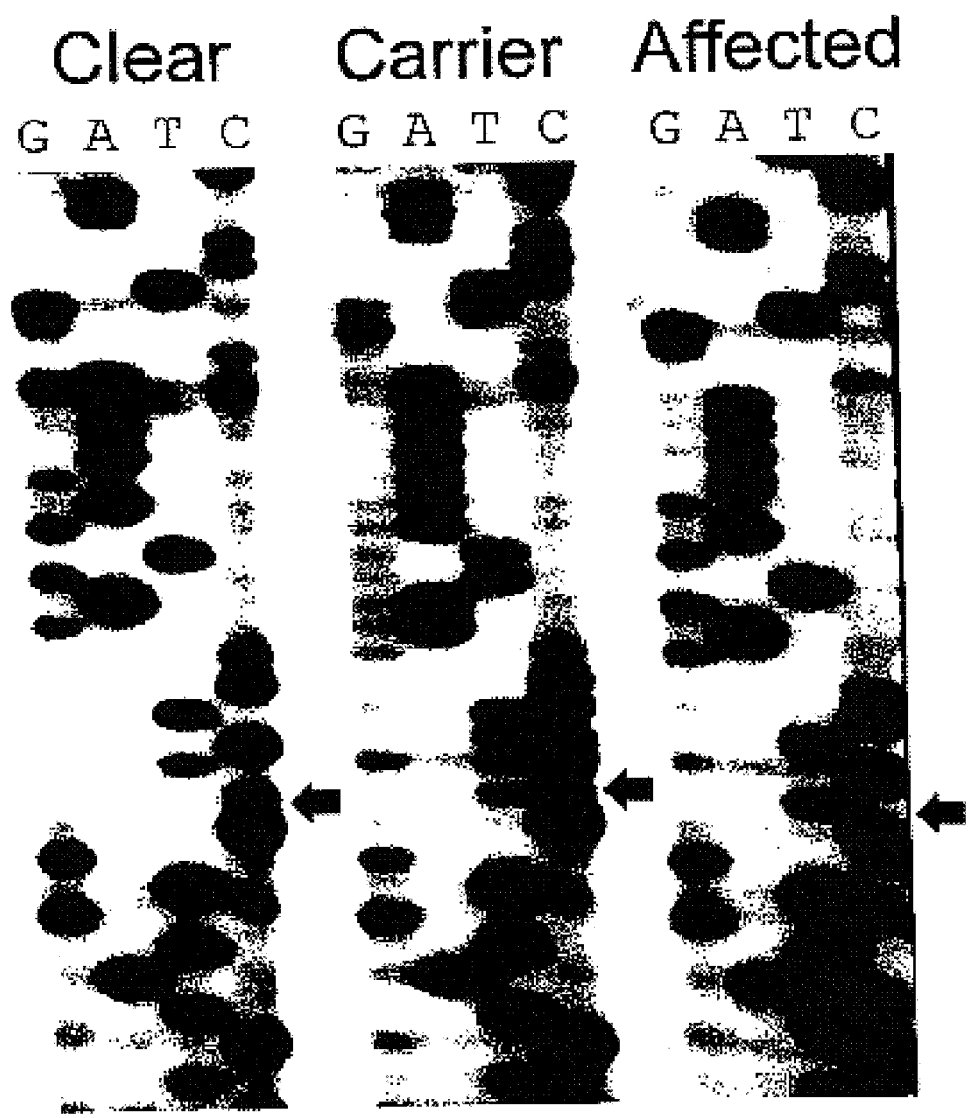
FIG. 3 provides nucleotide sequencing ladders for the von Willebrand's disease mutation region for normal (clear), carrier, and affected Scottish terriers, the sequences being obtained directly from PCR products derived from genomic DNAs in exon 4.

The cDNA encoding canine von Willebrand Factor (vWF) has been sequenced, and is set forth in FIGS. 1A–1C and SEQ ID NO: 1. The deduced amino acid sequence is set forth in FIGS. 2A–2C and SEQ ID NO: 2. In one embodiment, the mutation of the normal vWF gene which causes von Willebrand's Disease (vWD) in Scottish terriers, a deletion at codon 88 of the normal gene resulting in a frameshift, is provided. In another embodiment, a splice junction mutation at nucleotide position 7639 of the normal gene, which causes vWD in Doberman pinschers, Manchester terriers and Poodles, is provided. In yet another embodiment, a single base deletion at nucleotide position 937 of the normal gene, causing vWD in Shetland sheepdogs, is provided. The nucleic acid sequences of the present invention may be used in methods for detecting homozygous and heterozygous carriers of the defective vWF gene.

In a preferred method of detecting the presence of the von Willebrand allele in canines, DNA samples are first collected by relatively noninvasive techniques, i.e., DNA samples are obtained with minimal penetration into body tissues of the animals to be tested. Common noninvasive tissue sample collection methods may be used and include withdrawing buccal cells via cheek swabs and withdrawing blood samples. Following isolation of the DNA by standard techniques, PCR is performed on the DNA utilizing pre-designed primers that produce enzyme restriction sites on those DNA samples that harbor the defective gene. Treatment of the amplified DNA with appropriate restriction enzymes such as BsiE I thus allows one to analyze for the presence of the defective allele. One skilled in the art will appreciate that this method may be applied not only to Scottish terriers, Doberman pinschers, Shetland sheepdogs, Manchester terriers and Poodles, but to other breeds such as Dutch Kooikers, as well.

The presence of the von Willebrand allele in canines can also be detected utilizing ligation amplification reaction technology (LAR) known to those skilled in the art. LAR is a method analogous to PCR for DNA amplification wherein ligases are employed for elongation in place of polymerases used for PCR. Another alternate method for detecting the presence of the canine von Willebrand allele also known to those skilled in the art, is allele specific oligonucleotide hybridization, wherein an oligonucleotide of about 20 bp containing the contiguous nucleotides of the allele of interest is hybridized to the canine DNA.

The present invention provides breeders with an accurate, definitive test whereby the undesired, defective vWF gene may be eliminated from breeding lines. The current tests used by breeders are protein-based, and as noted previously, the primary difficulty with this type of test is the variability of results due to a variety of factors. The ultimate result of such variability is that an inordinate number of animals fall into an ambiguous grouping whereby carriers and noncarriers cannot be reliably distinguished. The present invention obviates the inherent limitations of protein-based tests by detecting the genetic mutation which causes vWD. As described in the Specific Examples, the methods of the present invention provide an accurate test for distinguishing noncarriers, homozygous carriers and heterozygous carriers of the defective vWF gene.

It will be appreciated that because the vWF cDNA of the present invention is substantially homologous to vWF cDNA throughout the canine species, the nucleic acid sequences of the present invention may be used to detect DNA mutations in other breeds as well. In addition, the canine vWF sequence presented herein potentially in combination with the established human sequence (Genbank Accession No. X04385, Bonthron, D. et al., *Nucleic Acids Res.* 14:7125–7128 (1986); Mancuso, D. J. et al., *Biochemistry* 30:253–269 (1989); Meyer, D. et al., *Throm Haemostasis* 70:99–104 (1993)), may be used to facilitate sequencing of the vWF gene and genetic defects causing vWD, in other mammalian species e.g., by using cross-species PCR methods known by those skilled in the art.

It is also within the contemplation of this invention that the isolated and purified nucleic acid sequences of the present invention be incorporated into an appropriate recombinant expression vector, e.g., viral or plasmid, which is capable of transforming an appropriate host cell, either eukaryotic (e.g., mammalian) or prokaryotic (e.g., *E. coli*). Such DNA may involve alternate nucleic acid forms, such as cDNA, gDNA, and DNA prepared by partial or total chemical synthesis. The DNA may also be accompanied by additional regulatory elements, such as promoters, operators and regulators, which are necessary and/or may enhance the expression of the vWF gene product. In this way, cells may be induced to over-express the vWF gene, thereby generating desired amounts of the target vWF protein. It is further contemplated that the canine vWF polypeptide sequence of the present invention may be utilized to manufacture canine vWF using standard synthetic methods.

One skilled in the art will appreciate that the defective protein encoded by the defective vWF gene of the present invention may also be of use in formulating a complementary diagnostic test for canine vWD that may provide further data in establishing the presence of the defective allele. Thus, production of the defective vWF polypeptide, either through expression in transformed host cells as described above for the active vWF polypeptide or through chemical synthesis, is also contemplated by the present invention.

The term "gene" as to referred herein means a nucleic acid which encodes a protein product. The term "nucleic acid"

refers to a linear array of nucleotides and nucleosides, such as genomic DNA, cDNA and DNA prepared by partial or total chemical synthesis from nucleotides. The term "encoding" means that the nucleic acid may be transcribed and translated into the desired polypeptide. "Polypeptide" refers to amino acid sequences which comprise both full-length proteins and fragments thereof. "Mutation" as referred to herein includes any alteration in a nucleic acid sequence including, but not limited to, deletions, substitutions and additions.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in *Current Protocols in Molecular Biology*, John Wiley & Sons, N.Y. (1989), 6.31–6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual*, Cold Spring Harbor Laboratory Press, Cold Spring N.Y., (1982), at pp. 387–389; see also Sambrook J. et al., *Molecular Cloning: A Laboratory Manual*, Second Edition, Volume 2, Cold Spring Harbor Laboratory Press, Cold Spring, N.Y. at pp. 8.46–8.47 (1989).

SPECIFIC EXAMPLE 1

SCOTTISH TERRIERS

Materials And Methods

Isolation of RNA. The source of the RNA was a uterus from a Scottish Terrier affected with vWD (factor level<0.1% and a clinical bleeder), that was surgically removed because of infection. Spleen tissue was obtained from a Doberman pinscher affected with vWD that died from dilated cardiomyopathy (factor level 7% and a clinical bleeder). Total RNA was extracted from the tissues using Trizol (Life Technologies, Gaithersburg, Md.). The integrity of the RNA was assessed by agarose gel electrophoresis.

Design of PCR primer sets. Primers were designed to a few regions of the gene, where sequences from two species were available (Lavergne, J. M. et al., *Biochem Biophys Res Commun* 194:1019–1024 (1993); Bakhshi, M. R. et al., *Biochem Biophys Acta* 1132:325–328 (1992)). These primers were designed using rules for cross-species' amplifications (Venta et al., "Gene-Specific Universal Mammalian Sequence-Tagged Sites: Application To The Canine Genome" *Biochem. Genet.* 34:321–341 (1996)). Most of the primers had to be designed to other regions of the gene using the human sequence alone (Mancuso, D. J. et al., *Biochemistry* 30:253–269 (1991)). Good amplification conditions were determined by using human and canine genomic DNAs.

Reverse Transcriptase-PCR. Total RNA was reverse transcribed using random primers (Bergenhem, N. C. H. et al., *PNAS* (*USA*) 89:8789–8802 (1992)). The cDNA was amplified using the primer sets shown to work on canine genomic DNA.

DNA Sequence Analysis. Amplification products of the predicted sizes were isolated from agarose gels by adsorption onto silica gel particles using the manufacturer's method (Qiagen, Chatsworth, Calif.). Sequences were determined using $^{33}$P-5' end-labeled primers and a cycle sequencing kit (United States Biochemical Corp., Cleveland, Ohio). The sequences of the 5' and 3' untranslated regions were determined after amplification using Marathon™ RACE kits (Clontech, Palo Alto, Calif.). Sequences were aligned using the Eugene software analysis package (Lark Technologies, Houston, Tex.). The sequence of the canine intron four was determined from PCR-amplified genomic DNA.

Design of a Diagnostic Test. PCR mutagenesis was used to create diagnostic and control BsiE I and Sau96 I restriction enzyme sites for the test. Amplification conditions for the test are: 94° C., 1 min, 61° C., 1 min, and 72° C., 1 min, for 50 cycles using cheek swab DNA (Richards, B. et al., *Human Molecular Genetics* 2:159–163 (1992)).

Population Survey. DNA was collected from 87 Scottish terriers from 16 pedigrees. DNA was isolated either from blood using standard procedures (Sambrook, J. et al., Cold Harbor Spring Lab, Cold Harbor Spring N.Y., 2nd Edition, (1989)) or by cheek swab samples (Richards, B. et al., *Human Molecular Genetics* 2:159–163 (1992)). The genetic status of each animal in the survey was determined using the BsiE I test described above.

Results

Comparison of the canine and human sequences. The alignment of the canine and human prepro-von Willebrand Factor amino acid sequences is shown in FIGS. 2A–2C (SEQ ID NO: 2). The location of the Scottish terrier vWD mutation is indicated by the "*". Potential N-glycosylation sites are shown in bold type. The known and postulated integrin binding sites are boxed. Amino acid numbers are shown on the right side of the figure. The human sequence is derived from Genbank accession number X04385.

Overall, 85.1% sequence identity is seen between the prepro-vWF sequences. The pro-region is slightly less conserved than the mature protein (81.4% vs. 87.5%). There were no other noteworthy percentage sequence identity differences seen in other regions of the gene, or between the known repeats contained within the gene (data not shown). Fourteen potential N-linked glycosylation sites are present in the canine sequence, all of which correspond to similar sites contained within the human sequence. The two integrin binding sites identified in the human vWF protein sequence (Lankhof, H. et al., *Blood* 86:1035–1042 (1995)) are conserved in the canine sequence as well (FIGS. 2A–2C; SEQ ID NO: 2). The 5' and 3' untranslated regions have diverged to a greater extent than the coding region (data not shown), comparable to that found between the human and bovine sequences derived for the 5' flanking region (Janel, N. et al., *Gene* 167:291–295 (1995)). Additional insights into the structure and function of the von Willebrand factor can be gained by comparison of the complete human sequence (Genbank Accession No. XO4385; Bonthron, D. et al., *Nucleic Acids Res.* 14:7125–7128 (1986); Mancuso, D. J. et al., *Biochemistry* 30:253–269 (1989); Meyer, D. et al., *Throm Haemostasis* 70:99–104 (1993)) and the complete canine sequence reported here.

The sequence for most of exon 28 was determined (Mancuso, D. J. et al., *Thromb Haemost* 69:980 (1993); Porter, C. A. et al., *Mol Phylogenet Evol* 5:89–101 (1996)). All three sequences are in complete agreement, although two silent variants have been found in other breeds (Table 1, exon 28). Partial sequences of exons 40 and 41 (cDNA nucleotide numbers 6923 to 7155, from the initiation codon) were also determined as part of the development of a polymorphic simple tandem repeat genetic marker (Shibuya, H. et al., *Anim Genet* 24:122 (1994)). There is a single nucleotide sequence difference between this sequence ("T") and the sequence of the present invention, ("C") at nucleotide position 6928.

Scottish Terrier vWD mutation. FIG. 3 shows nucleotide sequencing ladders for the vWD mutation region for normal (clear), carrier, and affected Scottish terriers. The sequences were obtained directly from PCR products derived from genomic DNAs in exon 4. The arrowheads show the location of the C nucleotide that is deleted in the disease-causing allele. Note that in the carrier ladder each base above the point of the mutation has a doublet appearance, as predicted for deletion mutations. The factor levels reported for these animals were: Normal, 54%; Carrier, 34%; Affected,<0.1%.

As a result of the deletion, a frameshift mutation at codon 88 leads to a new stop codon 103 bases downstream. The resulting severely truncated protein of 119 amino acids does not include any of the mature vWF region. The identity of the base in the normal allele was determined from an unaffected dog.

Development of a diagnostic test. A PCR primer was designed to produce a BsiE I site in the mutant allele but not in the normal allele (FIG. 4; SEQ ID NOS 3 and 10). The position of the deleted nucleotide is indicated by an asterisk. The altered nucleotides in each primer are underlined. The normal and mutant allele can also be distinguished using Sau96 I. The naturally occurring Sau96 I sites are shown by double underlines. The highly conserved donor and acceptor dinucleotide splice sequences are shown in bold type.

In order to ensure that the restriction enzyme cut the amplified DNA to completion, an internal control restriction site common to both alleles was designed into the non-diagnostic primer. The test was verified by digestion of the DNA from animals that were affected, obligate carriers, or normal (based on high factor levels [greater than 100% of normal] obtained from commonly used testing labs and reported by the owners, and also using breeds in which Type 3 vWD has not been observed). The expected results were obtained (e.g., FIG. 5). Five vWD-affected animals from a colony founded from Scottish terriers (Brinkhous, K. M. et al., *Ann. New York Acad. Sci.* 370:191–203 (1981)) were also shown to be homozygous for this mutation. An additional unaffected animal from this same colony was found to be clear.

It would still be possible to misinterpret the results of the test if restriction enzyme digestion was not complete, and if the rates of cleavage of the control and diagnostic sites were vastly different. The rates of cleavage of the two BsiE I sites were thus examined by partially digesting the PCR products and running them on capillary electrophores. The rates were found to be very nearly equal (the diagnostic site is cut 12% faster than the control site).

The mutagenesis primer was also designed to produce a Sau96 I site into the normal allele but not the mutant allele. This is the reverse relationship compared to the BsiE I-dependent test, with respect to which allele is cut. Natural internal Sau96 I sites serve as digestion control sites (shown in FIG. 4). The test using this enzyme produced identical genotypic results compared to the BsiE I for all animals examined (data not shown).

Figure 5:
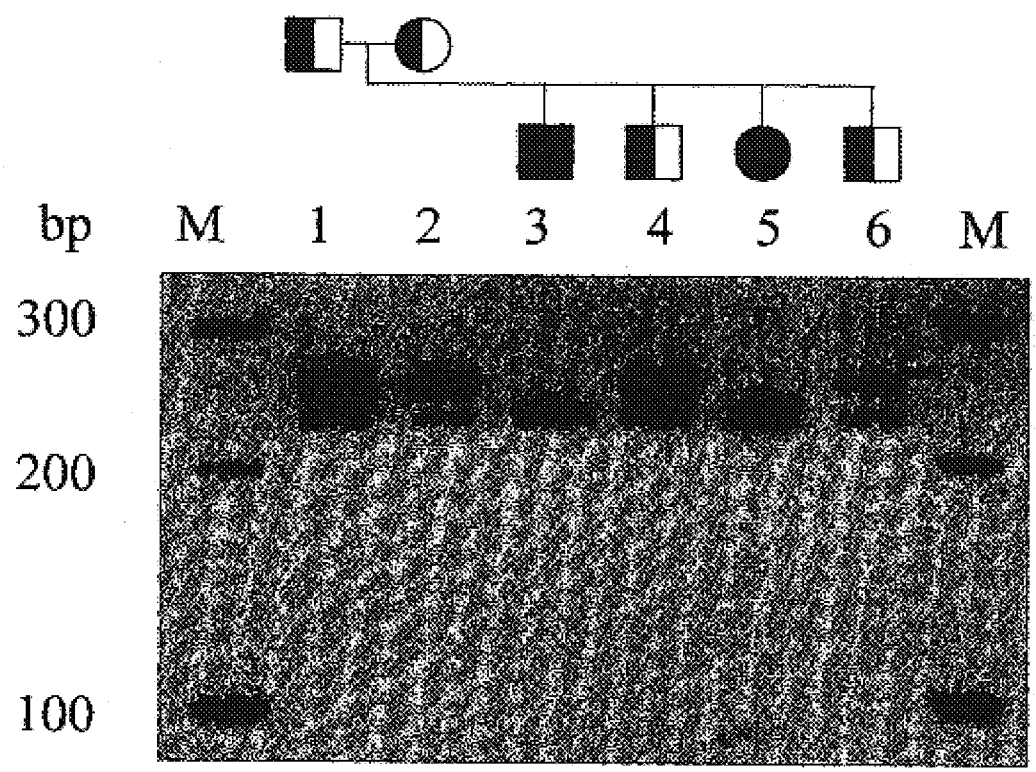
FIG. 5 shows the Scottish terrier pedigree, which in turn illustrates segregation of the mutant and normal vWF alleles.

Mendelian inheritance. One test often used to verify the correct identification of a mutant allele is its inheritance according to Mendel's law of segregation. Three pedigrees were examined in which the normal and mutant alleles were segregating, as shown in FIG. 5. Exon four of the vWF gene was PCR-amplified from genomic DNA. The PCR products were examined for the presence of the normal and mutant vWF alleles by agarose gel electrophoresis after digestion with BsiE I (see FIG. 5). The affected animals are homozygous for the mutant allele (229 bp; lanes 3 and 5). The other animals in this pedigree are heterozygotes (251 bp and 229 bp; lanes 1, 2, 4, and 6), including the obligate carrier parents.

TABLE 1

Differences Between Scottie And Doberman Pinscher Protein And Nucleotide von Willebrand Factor Sequences With Comparison To The Human Sequences

| Exon | A. A.[1] | Amino Acid | | | Codon | | |
|---|---|---|---|---|---|---|---|
| | | Human | Scottie | Doberman | Human | Scottie | Doberman |
| 5' UT[2] | nuc-35[3] | N/A[4] | N/A | N/A | N/A | A | G |
| 4 | 85 | S | S/F.Shift[5] | S | TCC | TCC/TC_ | TCC |
| 5 | 173 | M | R | K | ATG | AGG | AAG |
| 11 | 422 | S | T | T | TCC | ACA | ACC |
| 21 | 898 | C | C | C | TGC | TGT | TGC |

TABLE 1-continued

Differences Between Scottie And Doberman Pinscher
Protein And Nucleotide von Willebrand Factor Sequences
With Comparison To The Human Sequences

| | | Amino Acid | | | Codon | | |
|---|---|---|---|---|---|---|---|
| Exon | A. A.[1] | Human | Scottie | Doberman | Human | Scottie | Doberman |
| 21 | 905 | F | F | L | TTT | TTC | TTA |
| 24 | 1041 | S | S | S | TCA | TCA | TCG |
| 24 | 1042 | S | S | S | TCC | TCC | TCA |
| 28 | 1333 | D | D | E | GAG | GAG | GAG |
| 28 | 1349 | Y | Y | Y | TAT | TAT | TAC* |
| 42 | 2381 | P | L | P | CCC | CTG | CCG |
| 43 | 2479[6] | S | S | S | TCG | TCG | TCA |
| 45 | 2555 | P | P | P | CCC | CCC | CCG |
| 47 | 2591 | P | P | P | CCC | CCT | CCC |
| 49 | 2672 | D | D | D | GAT | GAT | GAC |
| 51 | 2744 | E | E | E | GAG | GAG | GAA |

[1]Amino acid residue position
[2]Untranslated region
[3]Nucleotide position
[4]Not Applicable
[5]Frameshift mutation
[6]Splice site mutation for Doberman pinscher, Manchester terrier and Poodle Boxed residues show amino acid differences between breeds
*This site has been shown to be polymorphic in some breeds The mature VWF protein begins in exon 18

The alleles, as typed by both the BsiE I and Sau96 I tests, showed no inconsistencies with Mendelian inheritance. One of these pedigrees included two affected animals, two phenotypically normal siblings, and the obligate carrier parents. The two parents were found to be heterozygous by the test, the two affected animals were found to be homozygous for the mutant allele, and the normal siblings were to be heterozygotes.

Population survey for the mutation. Cheek swabs or blood samples were collected from 87 animals in order to determine the incidence of carriers in the U.S. Scottish terrier population. Although an attempt was made to make the sample as random as possible, these dogs were found to come from 16 pedigrees, several of which are more distantly interconnected. This is due to some ascertainment bias, based on ownership (as opposed to phenotypic ascertainment bias). In these 87 animals, 4 affected and 15 carrier animals were found.

Discussion

These results establish that the single base deletion found in exon four of the vWF gene causes vWD in the Scottish terrier breed. The protein produced from the mutant allele is extremely short and does not include any of the mature vWF protein. Four Scottish terriers known to be affected with the disease are homozygous for the mutation. Five other mixed-breed dogs descended from Scottish terriers, and affected with vWD, are also homozygous for the mutation. No normal animals are homozygous for the mutation. Unaffected obligate carriers are always heterozygous for the mutation.

The gene frequency, as determined from the population survey, appears to be around 0.13 resulting in a heterozygote frequency of about 23% and expected frequency of affected animals of about 2%. Although the sample size is relatively small and somewhat biased, these data are in general agreement with the protein-based surveys (Stokol, T. et al., *Res Vet Sci* 59:152–155 (1995); Brooks, M., *Probl In Vet Med* 4:636–646 (1992)), in that the allele frequency is substantial.

All data collected thus far indicate that this mutation may account for essentially all of the von Willebrand's disease found in Scottish terriers. This result is consistent with the results found for other genetic diseases, defined at the molecular level, in various domestic animals (Shuster, D. E. et al., *PNAS (USA)* 89:9225–9229 (1992); Rudolph, J. A. et al., *Nat Genet* 2:144–147 (1992); O'Brien, P. J. et al., *JAVMA* 203:842–851 (1993)). A likely explanation may be found in the pronounced founder effect that occurs in domestic animals, compared to most human and wild animal populations.

Published data using the protein-based factor assays have shown that, at least in several instances, obligate carriers have had factor levels that would lead to a diagnosis of "clear" of the disease allele. For example, in one study an obligate carrier had a factor level of 78% (Johnson, G. S. et al., *JAVMA* 176:1261–1263 (1980)). In another study, at least some of the obligate carriers had factor levels of 65% or greater (Brinkhous, K. M. et al., *Ann. New York Acad. Sci.* 370:191–203 (1981)). In addition, the number of animals that fall into an equivocal range can be substantial. In one study, 19% of Scottish terriers fell in this range (50–65% of the normal vWF antigen level) (Stokol, T. et al., *Res Vet Sci* 59:152–155 (1995)). Thus, although the protein-based tests have been useful, the certainty of the DNA-based test described herein should relieve the necessity of repeated testing and the variability associated with the protein-based assays.

The mutation is present in the pre-vWF part of the molecule. This part of the molecule is processed off prior to delivery of the mature protein into the plasma. This pre-portion of the molecule is important for the assembly of the mature vWF protein (Verwiej, L. et al., *EBMO J* 6:2885–2890 (1987); Wise, R. J. et al., *Cell* 52:229–236 (1988)). With the Scottish terrier frameshift vWD mutation, neither this pre-portion nor any of the mature factor is ever produced, in keeping with the fact that no factor has ever been detected in the blood of affected dogs.

The determination of the complete canine vWF cDNA sequence will have an impact upon the development of carrier tests for other breeds and other species as well. Currently, Shetland sheepdogs (see Specific Example 3) and Dutch Kooikers are known to have a significant amount of Type 3 vWD (Brooks, M. et al., *JAVMA* 200:1123–1127 (1992); Slappendel, R. J., *Vet-Q* 17:S21–S22 (1995)). Type 3 vWD has occasionally be seen in other breeds as well (e.g., Johnson, G. S. et al., *JAVMA* 176:1261–1263 (1980)). All Type 3 vWD mutations described in humans to date have been found within the vWF gene itself. The availability of the canine sequence will make it easier to find the mutations in these breeds. In addition, at least some Type 1 mutations have been found within the human vWF gene, and thus Type 1 mutations may also be found within the vWF gene for breeds affected with that form of the disease. The availability of two divergent mammalian vWF cDNA sequences will also make it much easier to sequence the gene from other mammalian species using cross-species PCR methods (e.g., Venta et al., *Biochem. Genet.* 34:321–341 (1996)).

The test described herein for the detection of the mutation in Scottish terriers may be performed on small amounts of DNA from any tissue. The tissues that are the least invasive to obtain are blood and buccal cells. For maximum convenience, a cheek swab as a source of DNA is preferred.

SPECIFIC EXAMPLE 2

DOBERMAN PINSCHER

Materials and Methods

RT-PCR and DNA Sequence Analysis. RNA was isolated by using Trizol (Life Technologies, Gaithersburg, Md.) from the spleen of a Doberman pinscher that was affected with vWD (factor value of 7% of normal) and that had died from dilated cardiomyopathy. RT-PCR was performed as previously described using primers to the canine vWF cDNA. Most PCR products were determined directly using a cycle sequencing kit (Amersham Corp, Chicago, Ill.). A minor band containing the four base deletion (see Results) was subcloned into a plasmid vector prior to sequence analysis. The five kb intron 43 was amplified using a commercially available kit for long PCR (Boehringer-Mannheim, Indianapolis, Ind.). The cycling times and temperatures were as follows: initial denaturation, 93° C., 2 min; 10 cycles of 93° C., 15 sec, 62° C., 30 sec, 68° C., 4 min; 20 cycles of 93° C., 15 sec, 62° C., 30 sec, 68° C., 4 min with 20 additional sec per cycle. This was followed by a final extension at 68° C. for 7 min. The sequences of the primers used were: exon 43 (sense primer), 5'-TCTACCCTGTGGGCCAGTTC-3' (SEQ ID NO: 26), and exon 44 (antisense primer), 5'-GACCACCTCACAGGCAGAT-3' (SEQ ID NO: 27).

PCR-Based Mutation Test. PCR mutagenesis was used to create an Msp I site in the normal allele but not in the mutant allele. An internal Msp I digestion control site was also created by PCR mutagenesis within the anti-sense primer, whose target is within intron 43. The control site is contained within the amplification products of both alleles. The sequences of the primers are: diagnostic (sense) primer, 5'-CTGTGAGGACAACTGCCTGC_C-3' (SEQ ID NO: 28); and common (anti-sense) primer, 5'-TGGCCCTGAAC C_GGAAATTACTCAAG-3' (SEQ ID NO: 29) (the altered bases within each primer are underlined). A 'touchdown' PCR protocol was used for the amplification. The amplification conditions are: 94° C., 30 sec, 63 to 55° C., 40 sec, and 72° C., 50 sec, for the first 8 cycles, with the annealing temperature dropping one degree per cycle. Twenty-eight additional cycles were run, with the annealing temperature held at 55° C. The DNA was digested with Msp I after PCR amplification.

Population Survey. Owners who participated in a population survey supplied cheek swabs from their dogs for genotype analysis. Richards, B. et al., *Hum. Mol. Genet* 2:159 (1992). A number of these dogs had associated vWF values that were determined by various testing laboratories that provide this service to breeders.

Results

During the sequence analysis of the vWF mRNA from an affected Doberman pinscher, a significant nucleotide difference from the Scottish terrier sequence was discovered. This change was found at the last base of exon 43 (nucleotide 7437 from the initiation codon, at amino acid position Ser 2479; G in Scotties, A in the affected Doberman) (Table 1). Although this is a silent amino acid change, it causes the splice junction to be less similar to the mammalian splice junction consensus. Nakai, K. et al., *Gene* 141:171 (1994); Krawcsak, M. et al., *Genet.* 90:41 (1992). Just upstream of the normal splice junction is another sequence that also has significant similarity to the consensus, which is increased by the A at nucleotide position 7437 (FIG. 6; SEQ ID NOS: 14–17). The A at the end of exon 43 could cause the normal splice junction to be used less frequently, and that the upstream cryptic splice site becomes the one predominantly used. Comparison of the splice sites by a devised statistical method (Shapiro, M. B. et al., *Nucleic Acids Res.* 15:7155 (1987)) gave the following scores: normal splice position with the wild-type allele (G at 7536), 83.9; cryptic splice site with the wild-type allele, 60.6; normal splice position with the mutant allele (A at 7437), 72.2; cryptic splice site with the mutant allele, 70.5. Higher scores represent a greater likelihood of splicing potential. The scores for the normal and cryptic splice sites are quite different with the wild-type allele, but are very close with the mutant allele. These results support the probability of a decreased likelihood for splicing at the normal site, and an increased potential for splicing at the cryptic site with the mutant allele.

A faint RT-PCR band just below the major band from which the variant nucleotide had been detected was observed. This minor band was missing the four bases at the end of exon 43 as confirmed by sequence analysis (FIG. 7; SEQ ID NO: 18). The position of the four deleted bases is shown on the right side of FIG. 7 (SEQ ID NO: 18).

Figure 8:
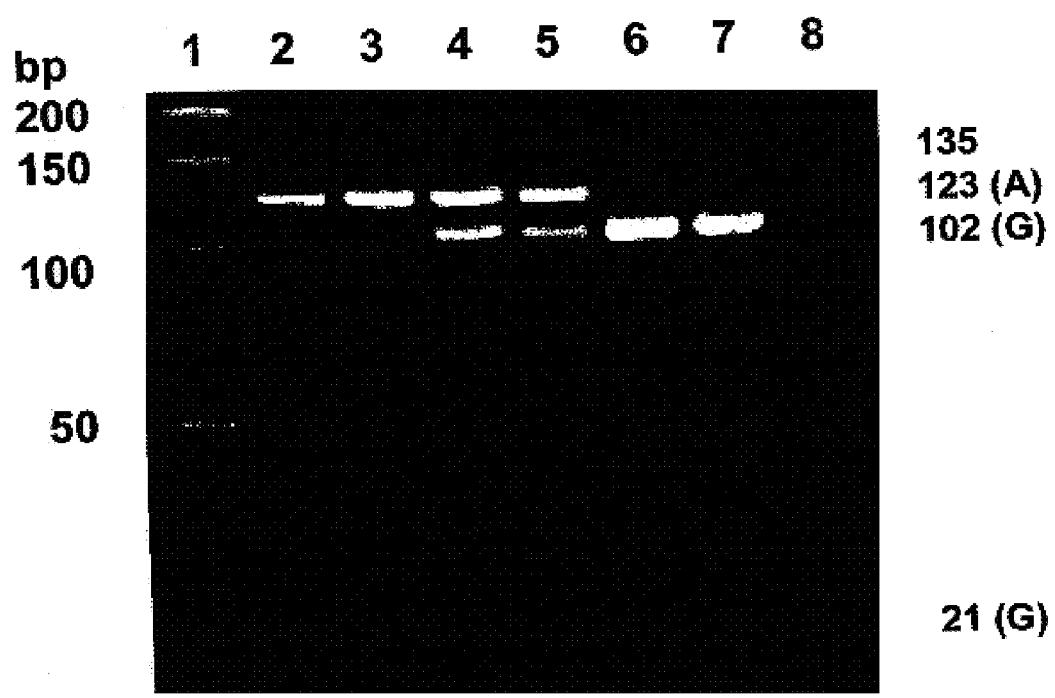
FIG. 8 is a photograph of an agarose gel showing representative results of the PCR-based diagnostic test.

A PCR-based test was developed to detect the nucleotide difference in genomic DNA as described herein in Materials and Methods. The results of the test for several animals with a spectrum of factor values yield a significant correlation between genotype and factor value as shown in FIG. 8. Lane 1 contains a 50 bp ladder as a size marker. The uncut PCR product is 135 bp (lane 8). Both alleles contain a common Msp I restriction site that serves as an internal digestion control. The mutant (A) and normal (G) alleles are represented by the 123 bp and 102 bp bands, respectively. Reported factor levels and deduced genotypic status for dogs represented in the additional lanes are as follows: 2, 12%, affected (AA); 3, 8%, affected (AA); 4, 39%, carrier (AG); 5, 68%, carrier (AG); 6, 125%, homozygous normal (GG); 7, 136%, homozygous normal (GG). A survey of 21 randomly ascertained animals with associated factor values showed a strong correlation between genotype and factor level as presented in the histogram of FIG. 9. The shaded boxes indicate predicted genotypes based on factor levels that are not consistent with the genotypes deduced from the PCR-based diagnostic test. Larger factor value-only surveys (Johnson et al., Vet. Clin. North Am. Small Anim. Pract. 18:195–229 (1988); Moser et al., Am. J. Vet. Res. 57:1288–1293 (1996); Stokol et al., Aust Vet J. 72:257–262 (1996)) indicate substantial overlap between genotypes based upon the protein-based methods. A larger survey on 67 additional Dobermans contained in 10 independently ascertained pedigrees was performed to obtain an estimate of the mutant allele frequency within the breed. Of the total of 88 animals, 40 were AA, 35 were AG, and 13 were GG. From these results, the A allele frequency was estimated to be 0.64.

Discussion

The splice junction mutation at the end of exon 43 is the cause of recessive Type 1 vWD found within the Doberman pinscher breed. The mutation decreases the similarity between the normal splice junction and the mammalian consensus while at the same time increasing the similarity of the cryptic splice site found just upstream of the normal splice site (FIG. 6; SEQ ID NOS: 14–17). The calculated Shapiro-Senapathy splice site values (Shapiro, M. B. et al., Nucleic Acids Res. 15:7155 (1987)) are very similar for the normal and cryptic splice sites when an A is present at nucleotide position 7536. The Shapiro-Senapathy calculation is probably not completely accurate in determining the relative amount of splicing that can occur between different sites. Therefore, it is not inconsistent to find that the cryptic splice site is used more often than the normal site, in the mutant allele.

Figure 7:
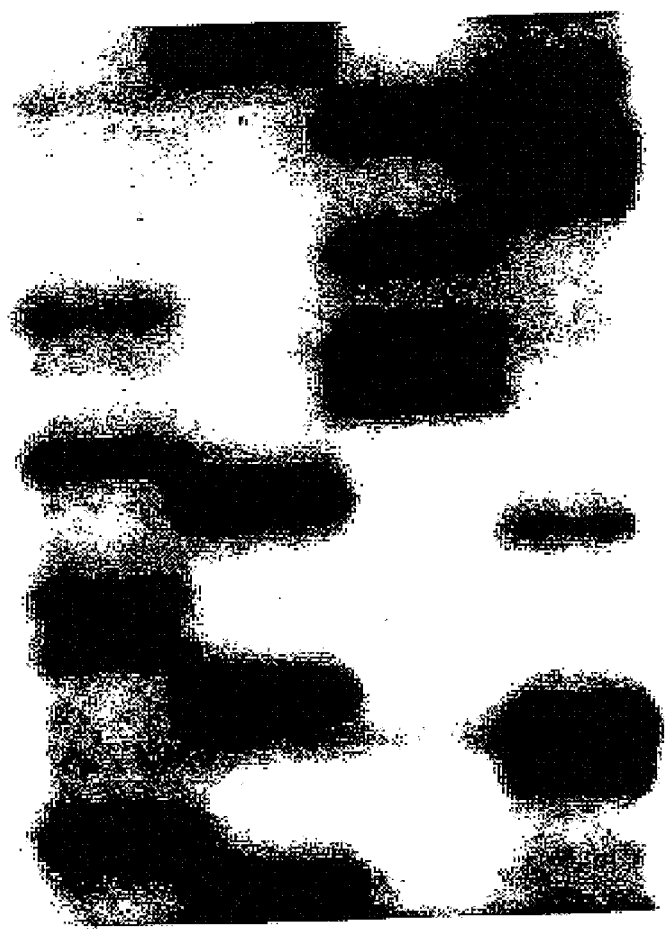
FIG. 7 is a photograph of a sequencing ladder showing the cryptic splice cite from the mutant allele (SEQ ID NO: 18)

The sequence of the minor amplification product seen just below the main amplification band exactly matches that predicted by the use of the cryptic splice site (FIG. 7; SEQ ID NO: 18). The fact that there is less cryptically spliced mRNA than normally spliced mRNA present in the cytoplasm can be explained by the relative instability of the cryptically spliced message. The cryptically spliced mRNA produces a shift in the translational reading frame, resulting in the formation of a premature stop codon. It is well known that mRNAs that produce truncated proteins are unstable, perhaps because ribosomes do not remain attached to the message to protect it from degradation by intracellular RNases or because of the incomplete assembly of splicosomes on mutant splice sites. Maquat, L. E., Am J Hum Genet 59:279 (1996). The average amount of vWF protein present in affected animals is roughly 10% of the normal canine value. Thus, each mutant allele should produce about 5% of the normal amount of vWF mRNA and protein. From this, it can be predicted that the average heterozygous Doberman should produce 55% of the average. canine vWF value. The vWF mRNA estimated in affected animals has been shown to be roughly 20% of normal by densitometry scans of northern blots. Meinkoth, J. H. et al., Am. J. Vet Res. 56:1577 (1995). This mRNA is predicted to consist primarily of the correctly spliced transcript.

Figure 9:
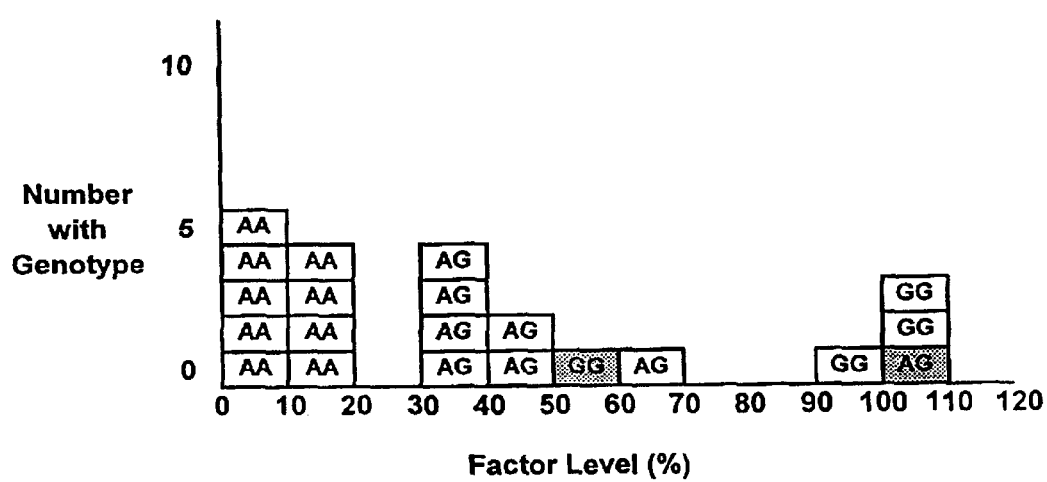
FIG. 9 is a histogram of genotypes versus reported vWF values.

The mutation has been shown to be linked to the vWF locus (FIG. 9 and Holmes, N. G. et al., J. Small An. Prac 37:307 (1996). Most human Type 1 vWD, in which there is a true clinical bleeding problem, appears to be inherited in a dominant, incompletely penetrant fashion. Ginsburg, D. et al., Blood 79:2507 (1992). Although a few Type 1 mutations have been found within the vWF locus (see, e.g., Siguret, V. et al., Hum. Genet 93:95 (1994); Eikenboom, J. C. J. et al., Blood 88:2433 (1996)), it has been argued that another locus or loci may also cause some Type 1 vWD. Ginsburg, D. et al., Blood 79:2507 (1992). In fact, one murine Type 1 vWD has been mapped to locus that is not linked to the vWF gene. Nichols, W. C. et al., Blood 83:3225 (1994). The data show that a least a proportion of Type 1 vWD in humans might also be caused by the exon 43 mutation, or other leaky splice junction mutations. The mode of inheritance for this type of mutation is recessive, but it might appear to be dominant in certain situations, such as that of the Doberman pinscher. The number of splice site mutations of the type described herein are significantly below the number that would be predicted to occur, suggesting that these types of mutations are more difficult to detect or have been overlooked in the past. Krawcsak, M. et al., Hum. Genet. 90:41 (1992). This might be because they produce a less severe phenotype than other types of mutations that cause a complete loss of function.

SPECIFIC EXAMPLE 3

SHETLAND SHEEPDOG

Figure 10:
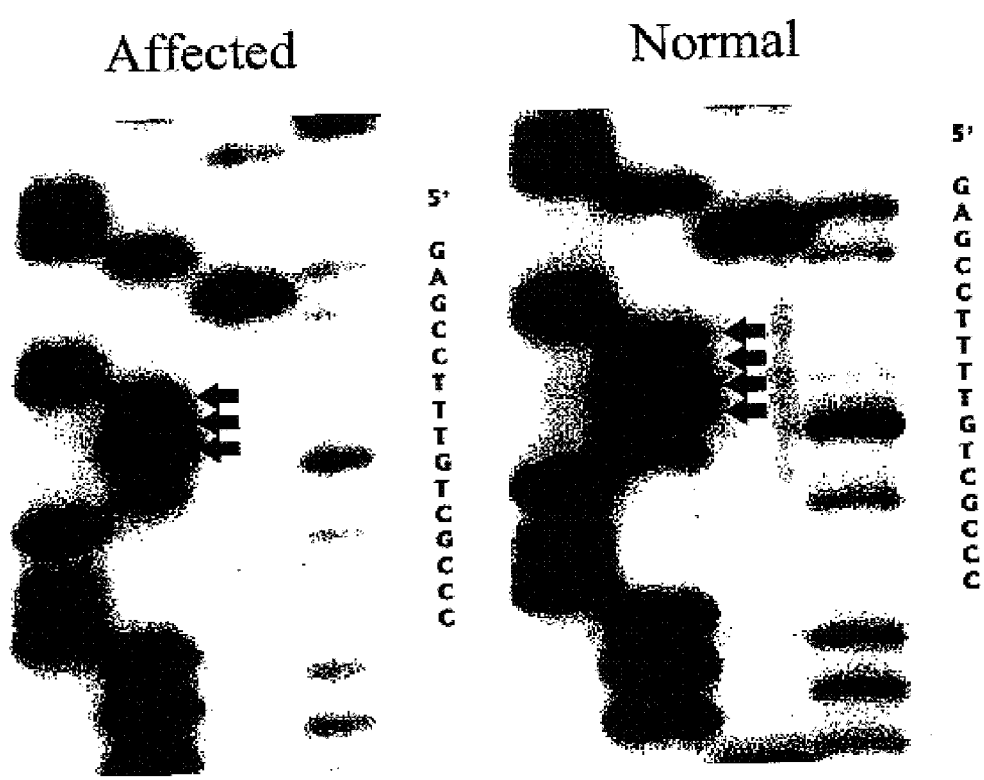
FIG. 10 is a photograph of a sequencing gel showing the mutation region between a vWD affected and a homozygous normal Shetland sheepdog (SEQ ID NOS: 19 and 20)
Figure 12:
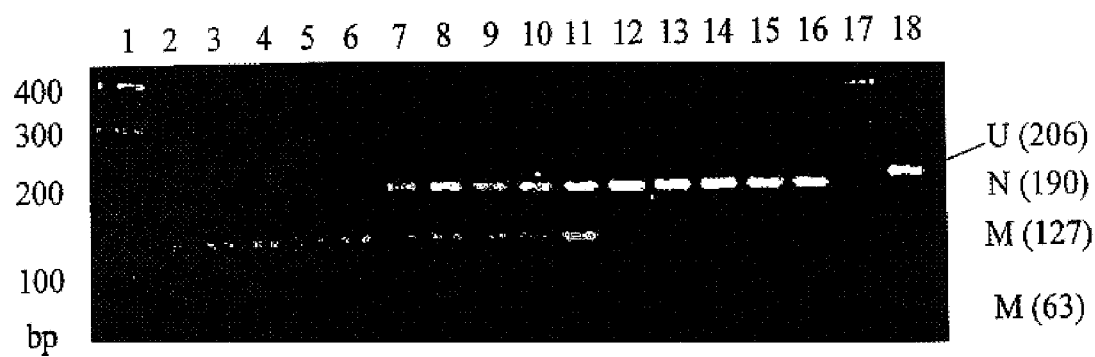
FIG. 12 is a photograph of an agarose gel showing the results of the diagnostic test for the Shetland sheepdog Type 3 vWD mutation.

Total DNA was isolated from material obtained from a spay of an affected Shetland sheepdog (Sheltie). This animal had been tested for the vWF antigen, and was reported to have a 0% value by a laboratory skilled in this testing (Diagnostic Laboratory, Comparative Hematology Section, College of Veterinary Medicine, Cornell University). The owner had decided to have the spay done after obtaining this result, and donated the removed tissues. The entire RT-PCR coding region of this mutant gene was sequenced as described in Specific Example 1, to identify the mutation that causes vWD. A mutation was found in the vWF gene that appears to be responsible for most or all of the type 3 vWD found in the Sheltie breed. A deletion of a single T was found at nucleotide position 735 of the encoding region (FIG. 10; SEQ ID NOS: 19 and 20). The arrows in FIG. 10 indicate the series of T nucleotides in which one T has been deleted in the DNA of the affected animal compared to the normal animal. This deletion, present in the equivalent of human exon 7, would cause a shift in the reading from of the vWF encoding region, and result in a severely truncated protein. A diagnostic test was designed to detect this mutation (FIG. 11; SEQ ID NOS: 21–25). The deletion causes the creation of an Mwo I restriction site and thus, the Mwo site is found in the mutant allele, but not in the normal allele. The sequence shown in FIG. 11 (SEQ ID NOS: 21 and 22) is that of the canine gene that corresponds to the human vWF exon 7. The single letter code for amino acids is shown above the nucleotide sequence and the primer sequences are shown below the gene sequence. The Mwo I sites are also indicated. An internal digestion control site is present in the non-diagnostic primer region. Reagent concentrations for this test were: 100 $\mu$M dNTPs, 50 mM KCl, 10 mM Tris-HCl (pH 8.3), 2 mM MgCl$_2$, 0.05 to 0.1 $\mu$g target DNA, 15 $\mu$M of each primer (SEQ ID NOS: 23 and 25), and 0.025 U Taq DNA polymerase. Cycling conditions were: 94° C., 4 min, one cycle, followed by 50 cycles of 94° C., 30 sec, 63° C., 40 sec, and 72° C., 40 sec. The relatively low Taq concentration (compared to generally accepted conditions) with the high number of cycles prevents the amplification of non-specific PCR bands. One microliter of Mwo I restriction enzyme (New England Biolabs, Inc.) and 2 µl of 50 mM MgCl$_2$ were added directly to the PCR reaction after amplification, and incubated at 60° C. for 1 hr. Digestion products were then observed after gel electrophoresis on a 1.5% agarose gel and the results shown in FIG. 12. Lanes 1 and 17 show a one hundred bp ladder. Lanes 2–6 show the results from an affected animal, lanes 7–11 show the results from a carrier animal, and lanes 12–16 show the results from a homozygous normal animal. Lane 18 shows an undigested control PCR product. The duplicate samples demonstrate the reproducibility of the test. Numbers on the left side of the gel show the sizes of the standard bands, and numbers on the right side of the gel show the sizes of the uncut product (U), the normal allele (N), and the two bands for the mutant allele (M).

A survey of Shelties was conducted to determine the frequency of the mutation within the U.S. population. Of a total of 103 animals, 14 were carriers, giving a carrier frequency of 13.6%. This frequency is less than the value of 28% reported for the breed in 1988 for 730 animals when using the factor antigen test. Brooks, M. et al., *J. Am. Vet Med. Assoc.* 200:1123–1127 (1992). One third of these carriers are thought to be due to Type 1 vWD also present in the breed. Still, the value of 13.6% would be lower than the calculated value of 18.7% from the antigen test. This difference could be due to either ascertainment biases in either study, a true decrease in the frequency of the disease in this breed, one or more additional Type 3 mutations in the breed, or a combination of these possibilities. Whatever the reason for the difference, most or all of the Type 3 disease in the Sheltie is probably caused by this one mutation. This is based on the understanding of the importance of the Founder effect (or populate sire effect) on the increase in the frequency of specific genetic diseases in purebred populations of domestic animals. A 17 member pedigree of Shelties, in which the mutation was segregating was tested for normal Mendelian inheritance of the allele. There were no differences from what would be expected under co-dominant inheritance of the two alleles.

SPECIFIC EXAMPLE 4

In an effort to find mutations that cause vWD in other canine breeds, affected animals were surveyed, as diagnosed by low levels of vWF antigen, for the three mutations set forth herein. In the case of the Manchester terrier breed, it was found that at least a portion of the affected animals had the identical mutation that causes vWD in the Doberman pinscher. The test described supra for the Doberman pinscher was utilized to test an affected Manchester terrier, plus several related animals. The affected animal was found to be homozygous for the mutant allele (Table 2). In addition, several animals who had vWF values in the carrier range were found to be carriers at the genotypic level.

TABLE 2

Manchester terrier vWF values vs. DNA genotype

| Dog | vWF value[a] | Genotype[b] |
|-----|----------|----------|
| MT1 | 200% | normal |
| MT2 | 76% | normal |
| MT3 | 42% | carrier |
| MT4 | 19% | carrier |
| MT5 | NT | carrier |
| MT6 | NT | carrier |
| MT7 | 10% | affected |

[a]Factor values as reported from a testing lab (Cornell CVM, Hematology Lab).
[b]Genotype for the leaky splice mutation originally found in the Doberman pinscher.

SPECIFIC EXAMPLE 5

In an effort to locate mutations that cause vWD in other canine breeds, affected animals as diagnosed by low levels of vWF antigen, were surveyed for the three mutations set forth herein. The test described supra for the Doberman pinscher was utilized and, in the case of the Poodle breed, it was found that the affected animals had the identical mutation that causes vWD in the Doberman pinscher. The affected animals were found to be homozygous for the mutant allele. In addition, several animals who had vWF values in the carrier range were found to be carriers at the genotypic level.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All patents and other publications cited herein are expressly incorporated by reference.

We claim:

1. A method for detecting a mutation in a nucleotide sequence encoding the polypeptide of SEQ ID NO: 2 in a canine DNA sample comprising the steps of:
   a) amplifying the DNA sample by polymerase chain reaction to produce polymerase chain reaction products, wherein the polymerase chain reaction uses primers that produce a restriction site in either a normal or mutant allele of the nucleotide sequence;
   b) digesting the polymerase chain reaction products with a restriction enzyme specific to the restriction site to produce DNA fragments; and
   c) detecting the DNA fragments, thereby detecting a mutation in the nucleotide sequence encoding the polypeptide of SEQ ID NO: 2.

2. The method of claim 1, wherein the primers are those of SEQ ID NOS: 10 and 11.

3. The method of claim 1, wherein the DNA fragments are detected by gel electrophoresis.

4. The method of claim 1, wherein the restriction enzyme is BsiEI.

5. The method of claim 1, wherein the restriction enzyme is Sau96 I.

6. A method of identifying a dog that is a carrier of vWD, comprising the step of determining whether the dog has a mutation in SEQ ID NO: 1, wherein the mutation is found at a nucleotide position selected from the group consisting of nucleotide positions 85, 937 and 7639.

7. The method of claim 6, wherein the determining step includes the step of amplifyifg the nucleotide sequence of SEQ ID NO: 1 or a portion thereof, from a DNA sample from the dog.

8. The method of claim 7, wherein the portion of the nucleotide sequence of SEQ ID NO: 1 that is amplified Exon 43, or a portion thereof.

9. The method of claim 6, wherein the mutation is at nucleotide position 85.

10. The method of claim 6, wherein the mutation is at nucleotide position 937.

11. The method of claim 6, wherein the mutation is at nucleotide position 7639.

12. The method of claim 10, wherein the portion of the nucleotide sequence of SEQ ID NO: 1 that is amplified is Exon 7, or a portion thereof.

13. The method of claim 9, wherein the portion of the nucleotide sequence of SEQ ID NO: 1 that is amplified is Exon 4, or a portion thereof.

* * * * *